US008579800B2

(12) United States Patent
Emura et al.

(10) Patent No.: US 8,579,800 B2
(45) Date of Patent: Nov. 12, 2013

(54) SYSTEMATIC CHROMOENDOSCOPY AND CHROMOCOLONOSCOPY AS A NOVEL SYSTEMATIC METHOD TO EXAMINE ORGANS WITH ENDOSCOPIC TECHNIQUES

(76) Inventors: Fabian Emura, Bogota (CO); Rodrigo Torres, Bogota (CO)

( * ) Notice: Subject to any disclaimer, the term of this patent is extended or adjusted under 35 U.S.C. 154(b) by 266 days.

(21) Appl. No.: 13/053,490

(22) Filed: Mar. 22, 2011

(65) Prior Publication Data

US 2012/0245415 A1 Sep. 27, 2012

(51) Int. Cl.
  *A61B 1/04* (2006.01)
  *A61B 1/00* (2006.01)
  *A61B 5/05* (2006.01)
  *A61F 11/00* (2006.01)
  *A61M 25/00* (2006.01)

(52) U.S. Cl.
  USPC ........... 600/117; 600/114; 600/424; 606/108; 604/528

(58) Field of Classification Search
  USPC ......... 600/117, 424, 137, 435, 109, 101, 114; 606/108; 604/528, 171
  See application file for complete search history.

(56) References Cited

U.S. PATENT DOCUMENTS

| | | | |
|---|---|---|---|
| 4,930,494 A * | 6/1990 | Takehana et al. | 600/145 |
| 5,099,846 A | 3/1992 | Hardy | |
| 5,297,346 A * | 3/1994 | Weiner | 33/512 |
| 5,390,661 A * | 2/1995 | Griffith et al. | 600/114 |
| 5,437,290 A * | 8/1995 | Bolger et al. | 128/898 |
| 5,617,858 A * | 4/1997 | Taverna et al. | 600/407 |
| 6,049,622 A | 4/2000 | Robb et al. | |
| 6,293,908 B1 * | 9/2001 | Fujikura et al. | 600/114 |
| 6,516,213 B1 | 2/2003 | Nevo | |
| 6,690,963 B2 | 2/2004 | Ben-Haim et al. | |
| 6,719,685 B2 * | 4/2004 | Fujikura et al. | 600/114 |
| 7,160,270 B2 * | 1/2007 | West et al. | 604/174 |
| 7,381,183 B2 | 6/2008 | Hale et al. | |
| 7,546,156 B2 | 6/2009 | Madden et al. | |
| 7,559,890 B2 | 7/2009 | Wallace et al. | |
| 8,439,866 B2 * | 5/2013 | Gaiser et al. | 604/96.01 |
| 2001/0056220 A1 * | 12/2001 | Fujikura et al. | 600/114 |
| 2002/0013512 A1 * | 1/2002 | Sendai et al. | 600/160 |
| 2002/0151871 A1 * | 10/2002 | Gaiser et al. | 604/510 |
| 2003/0208103 A1 * | 11/2003 | Sonnenschein et al. | 600/117 |
| 2004/0019254 A1 * | 1/2004 | Belson et al. | 600/146 |

(Continued)

FOREIGN PATENT DOCUMENTS

| | | |
|---|---|---|
| GB | 2.073.418 | 10/1981 |
| JP | 60217326 | 10/1985 |

*Primary Examiner* — John P Leubecker
*Assistant Examiner* — Ronald D Colque
(74) *Attorney, Agent, or Firm* — Michael I. Kroll

(57) ABSTRACT

An endoscopic screening system uses an apparatus has an endoscope with an upper/lower wheel and a right/left wheel for controlling bending of an endoscope tip within an organ being imaged; an intelligent mouthpiece adapted to precisely measure inclination of the endoscope using marks in degrees in both the novel mouth piece and in the new shaft; an endoscope shaft having both cross and longitudinal marks along a longitudinal length for digitalization of output to precisely obtain the length of insertion from a reference point to a tip of the endoscope; and an angulation device for measuring rotation of the upper/lower and right/left wheels. Every portion/part/side located within an organ is already assigned an alphanumeric code as part of the new nomenclature. The endoscopic screening system allows for imaging sequentially of an entire interior surface of a portion of the patient's gastrointestinal tract and image reconstruction of the surface with overlapping redundant pictures without image gaps.

1 Claim, 20 Drawing Sheets

(56) References Cited

U.S. PATENT DOCUMENTS

| | | | |
|---|---|---|---|
| 2004/0143160 A1* | 7/2004 | Couvillon, Jr. | 600/114 |
| 2005/0148847 A1* | 7/2005 | Uchiyama et al. | 600/407 |
| 2006/0149185 A1* | 7/2006 | Gaiser et al. | 604/77 |
| 2007/0135803 A1* | 6/2007 | Belson | 606/1 |
| 2007/0249901 A1* | 10/2007 | Ohline et al. | 600/117 |
| 2008/0161720 A1* | 7/2008 | Nicoson et al. | 600/567 |
| 2008/0306447 A1* | 12/2008 | West et al. | 604/174 |
| 2009/0062606 A1* | 3/2009 | Ueda et al. | 600/114 |
| 2009/0254079 A1* | 10/2009 | Edwards et al. | 606/33 |
| 2010/0063495 A1* | 3/2010 | Edwards et al. | 606/33 |
| 2010/0198096 A1* | 8/2010 | Colman et al. | 600/532 |
| 2010/0217197 A1* | 8/2010 | West et al. | 604/174 |
| 2010/0249775 A1* | 9/2010 | Gaiser et al. | 606/41 |

* cited by examiner

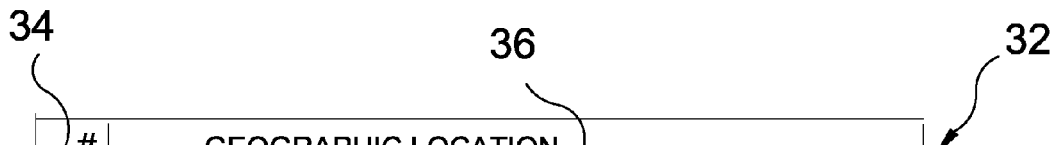

| # | GEOGRAPHIC LOCATION |
|---|---|
| 1 | NBI, HARD PALATE |
| 2 | NBI, HYPOPHARYNX |
| 3 | NBI, RIGHT PYRIFORM SINUS |
| 4 | NBI, LEFT PYRIFORM SINUS |
| 5 | NBI, ESOPHAGUS, SUPERIOR THIRD |
| 6 | NBI, ESOPHAGUS, MIDDLE THIRD |
| 7 | NBI, ESOPHAGUS, LOWER THIRD |
| 8 | NBI, ESOPHAGUS, HIATUS |
| 9 | WL, PYLORIC RING |
| 10 | WL, ANTRUM, ANTERIOR WALL |
| 11 | WL, ANTRUM, LESSER CURVATURE |
| 12 | WL, ANTRUM, POSTERIOR WALL |
| 13 | WL, ANTRUM, GREATER CURVATURE |
| 14 | WL, ANTRUM, MIDDLE-THIRD ANTERIOR WALL |
| 15 | WL, ANTRUM, MIDDLE-THIRD LESSER CURVATURE |
| 16 | WL, ANTRUM, MIDDLE-THIRD POSTERIOR WALL |
| 17 | WL, ANTRUM, MIDDLE-THIRD GREATER CURVATURE |
| 18 | WL, MIDDLE-THIRD ANTERIOR WALL |
| 19 | WL, MIDDLE-THIRD LESSER CURVATURE |
| 20 | WL, MIDDLE-THIRD POSTERIOR WALL |
| 21 | WL, MIDDLE-THIRD GREATER CURVATURE |
| 22 | WL, UPPER-THIRD, GREATER CURVATURE |
| 23 | WL, UPPER-THIRD, POSTERIOR WALL |
| 24 | WL, FORNIX |
| 25 | WL, UPPER-THIRD ANTERIOR WALL |
| 26 | WL, CARDIAS |
| 27 | WL, ESOPHAGEAL HIATUS IN RETROFLEXION |
| 28 | WL, UPPER-THIRD, LESSER CURVATURE |
| 29 | WL, MIDDLE-THIRD LESSER CURVATURE |
| 30 | WL, LOWER-THIRD LESSER CURVATURE |
| 31 | WL, ANGLE |
| 32 | WL, ANGLE, ANTERIOR WALL |
| 33 | WL, ANGLE, POSTERIOR WALL |

FIG. 3

| 34 | WL, DUODENAL BULB |
|---|---|
| 35 | WL, DUODENUM, SECOND PORTION |
| 36 | WL, DUODENUM, THIRD PORTION |
| 37 | NBI, PYLORIC RING |
| 38 | NBI, ANTRUM, ANTERIOR WALL |
| 39 | NBI, ANTRUM, LESSER CURVATURE |
| 40 | NBI, ANTRUM, POSTERIOR WALL |
| 41 | NBI, ANTRUM, GREATER CURVATURE |
| 42 | NBI, ANTRUM, MIDDLE-THIRD ANTERIOR WALL |
| 43 | NBI, ANTRUM, MIDDLE-THIRD LESSER CURVATURE |
| 44 | NBI, ANTRUM, MIDDLE-THIRD POSTERIOR WALL |
| 45 | NBI, ANTRUM, MIDDLE-THIRD GREATER CURVATURE |
| 46 | NBI, MIDDLE-THIRD ANTERIOR WALL |
| 47 | NBI, MIDDLE-THIRD LESSER CURVATURE |
| 48 | NBI, MIDDLE-THIRD POSTERIOR WALL |
| 49 | NBI, MIDDLE-THIRD GREATER CURVATURE |
| 50 | NBI, UPPER-THIRD, GREATER CURVATURE |
| 51 | NBI, UPPER-THIRD, POSTERIOR WALL |
| 52 | NBI, FORNIX |
| 53 | NBI, UPPER-THIRD ANTERIOR WALL |
| 54 | NBI, CARDIAS |
| 55 | NBI, ESOPHAGEAL HIATUS IN RETROFLEXION |
| 56 | NBI, UPPER-THIRD, LESSER CURVATURE |
| 57 | NBI, MIDDLE-THIRD LESSER CURVATURE |
| 58 | NBI, LOWER-THIRD LESSER CURVATURE |
| 59 | NBI, ANGLE |
| 60 | NBI, ANGLE, ANTERIOR WALL |
| 61 | NBI, ANGLE, POSTERIOR WALL |
| 62 | NBI, DUODENAL BULB |
| 63 | NBI, DUODENUM, SECOND PORTION |
| 64 | NBI, DUODENUM, THIRD PORTION |
| 65 | IC, DUODENUM, THIRD PORTION |
| 66 | IC, DUODENUM, SECOND PORTION |
| 67 | IC, DUODENAL BULB |
| 68 | IC, PYLORIC RING |

FIG. 4

| CORDINATE | MEASURES | GIVEN BY | COMMENTS / PICTURES |
|---|---|---|---|
| ONE | DEPTH OF PENETRATION OF THE SCOPE RELATIVE TO FIXED POINT IN A PATIENT | MOUTH PIECE (UPPER GI BRONCHOSCOPY ERCP) RECTAL PIECE (LOWER GI ), NAIRS (ENT) INTROITUS (VAGINA) ETC. ETC. | 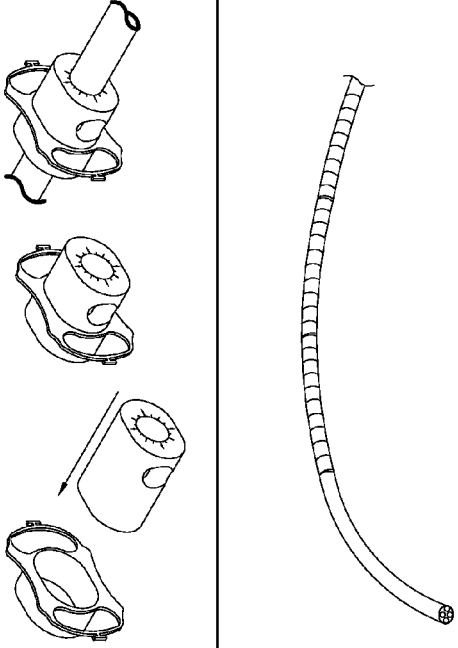 |
| TWO | ROTATION RELATIVE TO PATIENTS ANATOMICAL AXIS | ROTATION RELATIVE TO PATIENTS ANATOMICAL AXIS |  |
| THREE | POSITION OF THE MAIN INSTUMENTS SHAFT (IN CASE SCOPE HAS MORE THEN ONE | POSITION OF THE MAIN INSTUMENTS SHAFT (IN CASE SCOPE HAS MORE THEN ONE | NOT AVAILABLE IN CURRENT SCOPES BUT SOME PROTOTYPES HAVE SEVERAL ARMS, SO THIS CORDINATE WILL RECORD THE POSITION OF THE MAIN SHAFT AND THEN RELATIVE TO THIS ONE THE OTHER ARMS POSITIONS CAN BE CALCULATED AND RECORDED. |

FIG. 19A

| | | |
|---|---|---|
| FOUR - A<br>FOUR - B SECOND HEAD<br>FOUR - C THIRD HEAD<br>ETC. | U&D ROTATION OF THE SCOPES TIP | U&D WHEEL FOR EGD SCOPES PRODUCED TODAY AND THE ANGULATION DEVICE |
| FIVE - A<br>FIVE - B SECOND HEAD<br>FIVE - C THIRD HEAD ETC. | R&L ROTATION OF THE SCOPES TIP | R&L ROTATION OF THE SCOPES TIP AND THE ANGULATION DEVICE |
| SIX - A<br>SIX - B SECOND HEAD<br>SIX - C THIRD HEAD ETC. | AMOUNT OF AIR IN THE ORGAN (DISTANCE FROM SCOPE TIP TO ORGANS WALL) | SONAR PROBE OPERATOR MODIFIABLE COMPUTER ADJUSTED. | NOT AVAILABLE ON INSTUMENTS PRODUCED TODAY, CURRENTLY A SMALL PLASTIC CAP IS USED FOR ENDOSCOPISTS WHO DO MAGNIFYING ENDOSCOPY BUT NOTHING LIKE THIS EXISTS FOR REGULAR ENDOSCOPIC PROCEDURES |

FIG. 19B

SYSTEMATIC CHROMOENDOSCOPY AND CHROMOCOLONOSCOPY AS A NOVEL SYSTEMATIC METHOD TO EXAMINE ORGANS WITH ENDOSCOPIC TECHNIQUES

BACKGROUND OF THE INVENTION

1. Field of the Invention

The present invention relates generally to medical procedures and, more specifically, to system and apparatus for performing endoscopic procedures for internal organs, including stomach, colon, mouth, hypopharynx, larynx, duodenum, small intestine, urinary bladder, urethra, chest cavity, bronchioles, trachea, peritoneal cavity, middle ear. In this particular invention a standardized method is developed to prepare the area of interest, by using special lights, dyes, or any other technology, that will enhance the visibility of abnormalities, and thus increase early detection of disease. Also the test is standardized using a coordinate system either analog or digital that can increase reproducibility of the exam, and once digitalized can be transmitted to a remote place to allow for tele-medicine operations. In addition a new medical endoscopy nomenclature describe every part/portion located within a specific organ.

The application illustrates a specific embodiment of the invention, which is not intended to limit the invention in any manner.

2. Description of the Prior Art

There are other endoscopic diagnostic methods known in the art. While these techniques may be suitable for the purposes for which they where designed, they would not be as suitable for the purposes of the present invention as heretofore described.

Standard esophago/gastro/duodenoscopy (SEG) examines the upper gastrointestinal GI (hypopharynx, esophagus, stomach and duodenum). Colonoscopy examines the rectum, colon, terminal ileum. In spite of massive worldwide use of SEG and standard colonoscopy, gastric and esophageal and colorectal cancers are still leading causes of death in many countries. In the USA, gastric cancer accounts for about 7500 new cases each year, while colon cancer is the third cancer in frequency in both men and women. Colon cancer is a much more severe problem in the USA than gastric cancer. Multiple tests are available as options for CRC screening. While stool-based tests improve disease prognosis by detecting early stage treatable cancers (and possibly advanced adenomas), endoscopic or radiologic tests that visualize the gastrointestinal mucosa have the potential to also prevent cancer by detecting polyps that can be endoscopically removed prior to malignant transformation. Thus, endoscopy is superior to radiologic techniques since it is both diagnostic and therapeutic.

In both colon and gastric cancer (in most cases) patients have a long "preclinical phase" meaning the disease is present, but unless early detected through endoscopy with a biopsy of the site (which can be extremely hard to see and locate), the disease is undetectable. At this stage, there are no clinical manifestations, meaning the patient does not feel anything. This phase can last for years, and as such there is a great need to detect the disease and treat it at the earliest possible stage.

In regards to the upper GI tract, SEG reports usually diagnosis either two disease conditions: chronic gastritis (a benign inflammation of the stomach) or an advanced stage tumor mass (where no cure is possible). It is noteworthy that endoscopic diagnosis of early cancer lesions is extremely low in many countries, including the U.S. The reasons for this are twofold: massive screening like in Japan and one recently in Colombia do not exist in the U.S.; and the lack of a standardized medical procedure to examine the organs so all the organs' surfaces are seen and recorded (via photography, video or both), which allows for early detection and treatment. Some lesions can look very benign and early cancer can be very difficult to diagnose: small tumors can look like tiny mucosal depressions, discoloration of the mucosa or slight elevations of the surface and therefore are frequently misdiagnosed as benign disease states.

There is presently enough technology to re-design the way examination of the GI tract is done utilizing the present invention described here and all the existing technology to detect disease much earlier allowing the introduction and reinforcement of the concept of cure to GI tract malignancies. These present invention as described herein incorporates these changes.

Most authorities would agree that as of today, the "gold standard" for upper GI examination is standard SEG, and for colonic diseases is standard colonoscopy. Some trials have investigated the use of "virtual colonoscopy" (CT scan) but colonoscopy is currently considered the state of the art diagnostic tool. Current upper or lower endoscopies have several limitations, including high operator dependence. This translates into higher cost and fewer "operators" available at any given time, thus posing a significant limitation to mass screening campaigns, as illustrated in FIG. 12 which shows how the present invention will lower operator dependence and increase the number of individuals which can be screened via Systematic Chromoendoscopy (SCE) and Systematic Chromocolonoscopy (SCC).

Another limitation is the lack of standardization: no particular protocol is followed, no particular order is followed, and the information seen is generally not recorded permanently. This poses a huge problem, for example, a lesion that is not visible to one operator may be visible to other and vice versa. Localization of lesions is sometimes hard. Virtual colonoscopy has some standardization, such as a permanent record of the exam (the CT pictures) with each picture corresponding to an anatomical location. The present invention, however, introduces standardization to the manner in which endoscopic GI exams are performed.

Furthermore, the preparation for screening exams is not optimal. Despite the proven benefit of using dyes and special lights the current screenings are rarely done using these available technologies.

The above-described issues represent huge obstacles to early detection and mass screening initiatives, and allow for the loss of many lives, by losing the opportunity to catch the disease in the preclinical phase. As many countries, including the U.S., face the challenges of an aging population and the looming possibility of medical doctor shortages, the current healthcare delivery structure needs to change. The present invention implements technology that can allow for this transition, allowing better efforts towards prevention of preventable widespread metastatic cancer, from a localized tumor in the stomach or colon, or other areas/organs that could be accessible in the future by endoscopic instruments.

SUMMARY OF THE PRESENT INVENTION

A primary object of the present invention is to provide a system and apparatus for performing endoscopic procedures comprising a new endoscopic procedure, a new endoscopic terminology, a novel mouthpiece, a novel endoscope shaft and a novel way of mapping using simple coordinates.

Another object of the present invention is to provide a system and apparatus for performing endoscopic procedures wherein said new endoscopic procedure consisting of preparation of the mucosa and in combination the use of chromoendoscopy and new optical technology.

Yet another object of the present invention is to provide a system and apparatus for performing endoscopic procedures wherein new terminology improves communication in scientific journals.

Another object of the present invention is to provide a system and apparatus for performing endoscopic procedures utilizing a novel way of mapping using simple coordinates derived from an angulation device that attaches to an endoscope providing means for recording coordinates in positive and negative degrees for both left and right movement and up and down movement and having graduated markings on the endoscope shaft providing a longitudinal location for a given target location.

Additional objects of the present invention will appear as the description proceeds.

The present invention overcomes the shortcomings of the prior art by providing an improved method and apparatus for performing endoscopic procedures for internal organs, including colon, mouth, hypopharynx, larynx, duodenum, small intestine, urinary bladder, urethra, chest cavity, bronchioles, trachea, peritoneal cavity, middle ear and the like. The present invention comprises performing Systematic Chromoendoscopy (SCE) and/or Systematic Chromocolonoscopy (SCC) as an advanced endoscopic technique characterized by a detailed, sequential and systematic photographic/videographic record of the entire gastrointestinal surface examined during an endoscopic procedure. Similarly to a computerized axial tomography (CT-Scan) for the study of abdominal masses, SCE/SCC performs an intraluminal scanning of the entire upper/lower gastrointestinal tract.

The foregoing and other objects and advantages will appear from the description to follow. In the description reference is made to the accompanying drawing figures, which form a part hereof, and in which is shown by way of illustration specific embodiments by which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIG.S

In order that the invention may be more fully understood, it will now be described, by way of example, with reference to the accompanying drawings in which:

FIG. 3 is a chart exemplifying universal terminology for the upper GI tract.

FIG. 4 is a continuation of the chart exemplifying universal terminology for the upper GI tract.

FIG. 19A-19B is a chart of the coordinate system of the present invention.

DESCRIPTION OF THE REFERENCED NUMERALS

Figure 1:
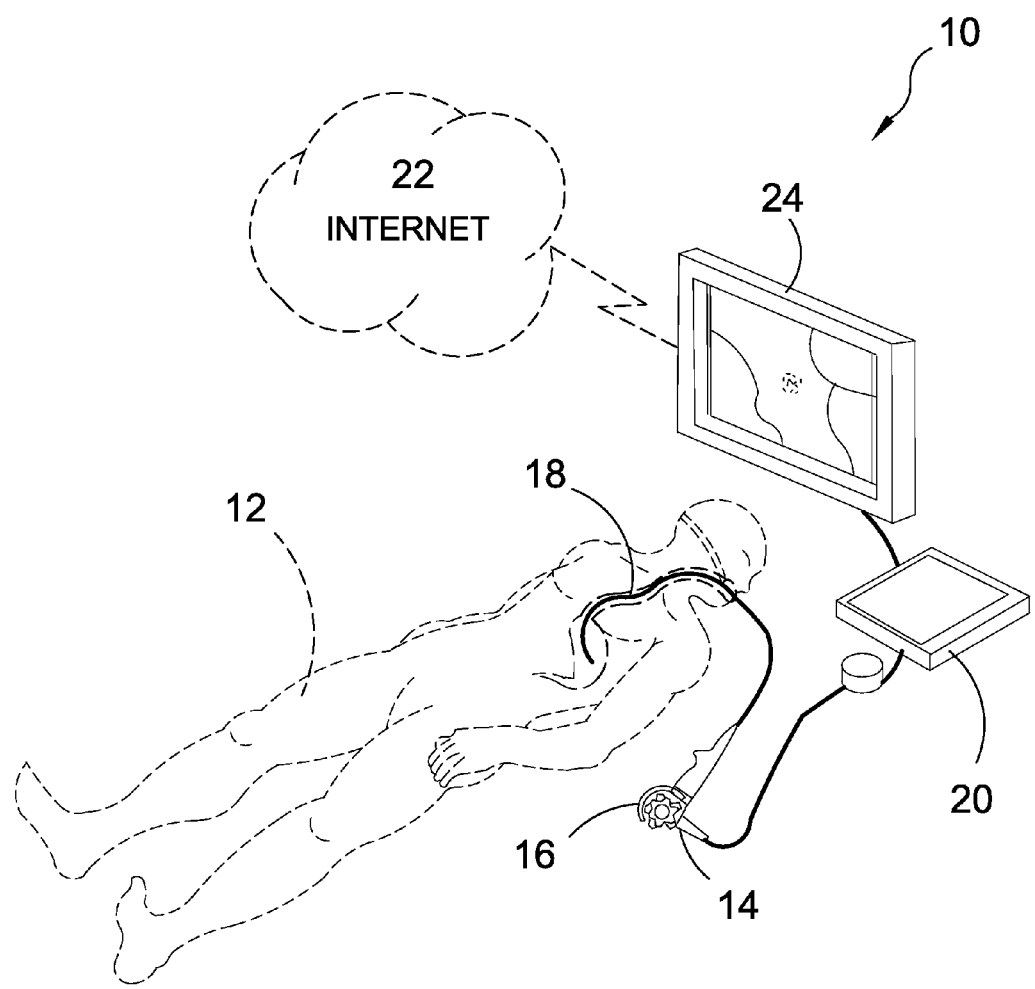
FIG. 1 is an illustrative view of the present invention in use.

Turning now descriptively to the drawing figures, in which similar reference characters denote similar elements throughout the several views, the figures illustrate the Endoscopic System and Apparatus of the present invention. With regard to the reference numerals used, the following numbering is used throughout the various drawing figures.

10 Endoscopic System of the present invention
12 patient
14 endoscope
16 angulation adapter
18 graduated endoscope shaft
20 processor
22 internet
24 display
26 graduation degree markers
28 up/down wheel
30 left/right wheel
32 example of standardized chart by areas
34 example terminology reference number
36 example terminology location descriptor
38 intelligent mouthpiece
40 standard mouthpiece
42 sleeve
44 inclination degree marks on 38
45 lateral orifice
46 shaft
48 graduated marks on 46
50 sagittal plane
52 coronal plane
54 transverse plane
56 graphical plot
58 invasive cancer
60 localized cancer
62 number of individuals screened
64 operator dependence
66 higher operator dependence
68 lower operator dependence
70 prior art imaging system 72 imaging system of the present invention
74 prior art images
76 non-imaged portions of screened organ
78 images taken with the imaging system of the present invention
80 overlapping portions of 78
82 expert endoscopic surgeon
84 cure
86 expert screeners—M.D.
88 expert screeners—non-M.D.
90 other expert screeners
92 resection
94 master endoscopic surgeon
96 remote location
98 screening expert supervisor
100 screener experts
102 population to be screened

DETAILED DESCRIPTION OF THE PREFERRED EMBODIMENT

The following discussion describes in detail one or more embodiments of the invention. This discussion should not be construed, however, as limiting the invention to those particular embodiments, practitioners skilled in the art will recognize numerous other embodiments as well. For definition of the complete scope of the invention, the reader is directed to appended claims.

The present invention provides a new process for performing examination of the GI tract via Systematic Chromoendoscopy (SCE) and/or Systematic Chromocolonoscopy (SCC) as an advanced endoscopic technique characterized by a detailed, sequential and systematic photographic record (or video) of the entire gastrointestinal surface examined during an endoscopic procedure. Similarly to a computerized axial tomography (CT-Scan) for the study of abdominal masses, SCE/SCC performs an intraluminal scanning of the entire upper/lower gastrointestinal tract (hypopharynx, esophagus, stomach and duodenum up to the third portion for SCE, and rectum, colon, terminal ileum for SCC). If a lesion is found in certain area/quadrant (given by the coordinate system described hereinbelow) that lesion is easily localized by a second endoscopist, and can be monitored over time.

The sequence of steps for practicing the present invention for SCE/SCC are as follows:

1) Appropriate selection of the patient/population: this is a test for screening individuals, in which the cancer risk justifies the cost of the intervention. These individuals are in stable medical condition; it is not for emergency procedures but some principles could be used in the future for emergency procedures (particularly the recording of the photographic data and coordinates of lesions, if found).

2) Appropriate cleaning of the mucosa: for upper GI, this is done according standard protocol and administered before the procedure, consisting of a mix of a) an appropriate fasting period, b) thorough cleansing of the mucosa, for example, with an enzyme (pronase) or a mucolytic agent like n-acetyl cysteine, or any other combination that is safe and effective for mucosal cleansing, c) through removing saliva bubbles, for example, a polymer composed of alternating silicon and oxygen atoms like dimethylpolysiloxane. This practice substantially improves visualization of the gastric mucosa under conventional lighting, NBI and conventional chromoendoscopy so no lesions are missed.

3) With the patient in left lateral decubitus position and the level of the bed at approximately the hip level of the examiner, endoscope insertion is performed followed by sequential and systematic examination and photography/videography of the organs to be examined.

4) Image reconstruction of the surface with overlapping redundant pictures with white light, NBI (hemoglobin narrow band light—trademarked by Olympus®), and/or other type of narrow band light, and dyes. The dyes can be regular "old fashioned" dyes (not molecule specific), or dyes that target specific chemicals, including proteins or part of proteins called "epitopes" which means that this test could use in the future monoclonal antibodies to assist is localization of disease. Monoclonal antibodies are used today for treatment of many types of cancer, they could be used in the future to aid in localizing tumors with endoscopic procedures.

An important embodiment of the present invention requires that the pictures need to be redundant and overlapping so that no areas are missed, allowing for less trained personnel to perform the exam, while maximizing the time the expert endoscopic surgeon (EES) or master endoscopic surgeon (MES) is used.

5) Examination by an expert screener for diagnosis and report and then if needed by an expert endoscopic surgeon (EES). If needed, a "master" endoscopic surgeon (MES) can review the case and reassess the patient.

6) Endoscopic submucosal dissection or any other endoscopic procedure aiming cure performed by an EES or MES depending on the case complexity followed by cure or further medical follow up.

7) Referral to a surgeon for a wide resection if necessary, and/or follow up by oncology treatment.

8) Follow up appointment in a number of months determined by the expert gastroenterologist and/or endoscopic surgeon according the patient's risk.

In summary, SCE and SCC include the use of a mix of substances that cleans the stomach like Pronase (a proteolytic enzyme), N-acetyl cysteine (breaks disulfide bonds in mucopolysacharides), dimethylpolysiloxane (DMP) (to dissolve saliva bubbles), but it could be any other proteolitic/mucolytic/lipolytic enzyme, a detergent or any other chemical substance that can clean the mucosa in a satisfactory way and it is safe and easy to obtain and produce, thus allowing excellent preparation of the organ for a systematic examination.

The present invention substantially improves visualization of the organ's mucosa under conventional lighting, NBI and conventional chromoendoscopy, a practice superior to what is currently done today.

In addition, SCE and SCC uses the NBI system, an internationally accepted technique that uses a particular light wavelength to enhance imaging of the erythrocytes (red blood cells)—making them more visible—and thus, allows for detection of very small (2 to 3 mm) cancer lesions. Finally, SCE uses also conventional chromoendoscopy (indigo carmine, Lugol® or any other colorant/dye that enhances the microanatomy of the stomach or colon) providing remarkable enhancement of the surface microanatomy of the esophagus, stomach, colon and provides the endoscopist with a much better view of the lesion for which to perform biopsy/resection/burning or to destroy in any other form the lesion in order to diagnose/cure/palliate symptoms in a given patient. Use of the present invention has found that SCE plus premedication, NBI and chromoendoscopy is effective in reducing the risk of missing small gastric tumors in a large proportion of patients. While some medical articles speculate that NBI will replace chromoendoscopy these two technologies, one older and inexpensive (chromoendoscopy) and the other newer and expensive (NBI) are more likely complementary to each other with their own strengths and weaknesses. Therefore during SCE both are used, and SCE/SCC employed according to the present invention can also incorporate any new technologies that will increase early detection.

The coordinate system consists of measurement of several important parameters that will increase reproducibility of the test while reducing the operator dependence of the exam. As more technology is embedded in the instrument, the exam becomes much easier to perform, allowing for lower cost per exam and a wider population screened. Once finished, the serial pictures are evaluated individually or by areas or fused forming a panoramic view of the organ's surface, if desired, and presented/transmitted to the EES/MES for advice and or treatment.

As employed in the method of the present invention, the coordinate system includes the following steps.

1) Measurement of the depth of insertion of the new shaft device. Once a lesion is located the depth of insertion is measured observing the number of centimeters inserted having as cut off the edge of the novel mouthpiece. The final depth of insertion is 1 cm longer than the conventional measure since the edge of the novel mouthpiece is located 1 cm proximal (the distance from the incisor teeth to the edge of the novel mouth piece). Initially analog, this can be quantified manually or digitally and in both cases recorded. It can also be transmitted to a remote location.

2) Measurement of the angle of rotation of the new shaft device relative to the new mouth piece. This is accomplished putting together the longitudinal line of the new shaft device with the grades matched in the novel mouthpiece. This can be quantified manually or digitally and in both cases recorded. It can also be transmitted to a remote location.

3) Measurement of the degree of rotation of each of the endoscope wheels controls. This is done with the angulation device but could be done with electronic sensors located in the endoscope itself. For standard upper GI endoscopes, this means recording the position in grades of the u/d and r/l wheels (2 wheels for most current endoscopes). For newer endoscopes being developed (3 or more wheels, several arms) this means the recording of information of the endoscope main shaft and of each of the endoscope arms. This can be quantified manually or digitally and in both cases recorded. It can also be transmitted to a remote location.

4) Monitor and maintain proper organ air distension. For the GI tract, the amount of air in the organ is important as it can make a lesion be closer if there is less air or farther, if there is more air. This applies particularly to lesions in the stomach when the scope tip might be at an angle that approaches 90 degrees from the shaft. The distance to the organ's wall may also be important in the bladder and other body cavities. At this time being completely operator dependent this can be also handled with assist of, for example, a CO2 insufflator (or any other gas) and an incorporated device that measures the amount of intra luminal CO2/pressure CO2 within a cavity or a small sonar tip that ensures the right amount of air is present at all times (and it can be modified by the operator as well). This can be quantified manually or digitally and in both cases recorded. It can also be transmitted to a remote location. It is referenced in the coordinate system as coordinate six (6))

5) Once the information is obtained, it can be digitalized and evaluated/transmitted allowing for a remote operator to be able to assist the EES or MES in a surgery. In this regard, recent studies have demonstrated that physicians with no endoscopic experience and limited training were able to detect, with NBI, cancerous lesions, with the same frequency as top experts with white light. This enables the implementation of wider screening campaigns with lower trained staff, if clinically validated, this would greatly reduce costs. The present invention incorporates changes that will allow this to happen. Key features of the present invention incorporate the coordinate system and current imaging technology and reconstruction of the organ's surface with software which allows for less operator dependence, lower cost and overall higher impact on society as a whole. This opens the door for the training and creation of a new medical specialties, and training of technologists to reduce cost and allow the mass application of these examinations. Therefore standardization of endoscopic examinations in general will facilitate learning, reproduction and systematization, in the GI tract, bladder, vagina, nose, throat, lungs, and other organs that are examined today or can potentially be examined with these instruments, while making it possible for everybody to communicate more efficiently in the medical community.

The present invention comprises a novel method and endoscopic system employing an "intelligent" mouthpiece, a redesigned shaft and angulation device.

The mouthpiece of the present invention provides an easy and reproducible way (even for beginners or non-endoscopists) of performing SCE and to properly identify target areas. Preferably, the mouthpiece has marks at every degree starting at 0 and going to 360, in a clockwise progression with 0 degrees oriented at the front of the patient in an anatomical plane, and/or further markings at 0, ±90, ±180±90 degrees. It measures the grade of inclination of the endoscope using the patient as reference (this determines either a natural or handmade axis view). It measures 1 cm from the proximal edge of the standard mouth piece to its own proximal edge. The mouthpiece is initially designed to fix in a standard mouthpiece and incorporates a lateral orifice for drainage or suctioning and is reusable after standard cleaning procedures. Optionally, the mouthpiece can incorporate a simple electronic device that would digitally measure the inclination and depth of the tip of the endoscope. The orifice in the mouth piece is larger than the scope allowing for easy operation The electronic endoscope of the present invention includes a redesigned shaft. Marks on the endoscope are situated, for example, every 1 centimeter (analog) or 1 millimeter (digital), along the longitudinal length of the shaft for digitalization of output to the processor, are useful to precisely obtain the length of insertion from the reference point (proximal edge of the novel mouth piece) to the lesion. In addition, a longitudinal mark at the tip and along the shaft of the endoscope allows for determination of angulation grades by matching the longitudinal shaft mark with the one located in the mouthpiece and is useful to measure the inclination in degrees at any moment during the examination (when employed in combination with the above-described mouthpiece of the invention). The orifice in the mouth piece is larger than the scope allowing for easy operation The angulation device measures the rotation of the upper and lower (u/d), and right and left (r/l) wheels. A round plastic disposable device with marks in grades located parallel and preferably between the up-down/left-right wheels gives the exact degree of wheels' bending, or deflection. The angulation device is located on the head of the endoscope, close to but separated from the wheels facilitating observation of the grades, and stands in a position that avoids contact with the endoscopist's fingers, for example by having a generally C-shape. The bending determines the movements (left-right and up-down bending) of the endoscope's tip within the organ. The wheels' movement releases electronic/magnetic/echo/internet signals that are taken up to a processor that reconstitutes all this information into a tridimensional image. Deflection is preferably quantified as 0° to +45°+90° and 0° to −45°−90°. The round shaped disposable device can be replaced by short lines incorporated into the wheels or to the head of the endoscope at the same degrees. The endoscopic system of the present invention allows exact description and anatomical location of a lesion by measuring grades of inclination, depth of insertion and tip positioning.

The present invention integrates the inventive SCE/SCC protocol and coordinate system with current endoscope technology, and includes endoscopic systems of coordinates which are digitalized so that the instrument is "smart" allowing for it to monitor its position and provide feedback to the operator. Also all the coordinate information can be recorded in real time in each picture or frame (e.g., each millisecond) of video. Once digitized, the data can be transmitted to a remote location for analysis and storage.

Analog or digital SCE/SCC is accomplished by following a standardized process of insertion, manipulation and retrieval of the scope by using angles, scope's rotation, natural axis, anatomical landmarks, depth of insertion, imaging and information registration. SCE/SCC is simple and easy to learn even for beginners or non-endoscopists. The present invention also incorporates new terminology for SCE/SCC, as for the first time in medical endoscopy every small segment of the imaged organ is alphanumeric coded. An exact description and anatomical location of areas/lesions are further provided via identification of angles, degrees of inclination and length of insertion of the endoscope during the endoscopic examination.

For the first time in medical endoscopy both a new nomenclature of the areas examined by endoscopy (every small segment is alphanumeric coded) as well as angles, degrees of inclination and length of insertion are incorporated to an endoscopic examination for exact description and geographic location of areas/lesions. Specific names and numbers describe organ's sub-regions and small areas within each region (about every 1.5-2.5 square centimeters segments with overlapping pictures eliminating blind spots). SCE uses anatomic landmarks, geographic identification of small areas by naming every point observed in an endoscopic view (seen the endoscopic circumference like a round clock), reports the depth of insertion based of the endoscope length and uses natural or handmade endoscopic axis or angles (hand-manipulated from outside by moving the endoscope's wheels or by endoscopist hand-turning).

Some of the applications of this new medical terminology is to report/describe SCE, to record abnormalities (if any), to precisely locate a condition or an early lesion (other examiner can easily find it), to effectively design the way of endoscopic removal of a cancer and for effective follow up even for a different examiner. The sequence, names and numbers of each segment is describe as follows:

1. NBI, hard palate
2. NBI, Hypopharynx
3. NBI, Right Pyriform sinus
4. NBI. Left Pyriform sinus
5. NBI, Esophagus, superior third
6. NBI, Esophagus, middle third
7. NBI, Esophagus, lower third
8. NBI, esophageal hiatus
9. WL, Pyloric ring
10. WL, Antrum, anterior wall
11. WL, Antrum, lesser curvature
12. WL, Antrum, posterior wall
13. WL, Antrum, greater curvature
14. WL, Antrum-middle-third anterior wall
15. WL, Antrum-middle-third lesser curvature
16. WL, Antrum-middle-third posterior wall
17. WL, Antrum-middle-third greater curvature
18. WL, Middle-third anterior wall
19. WL, Middle-third lesser curvature
20. WL, Middle-third posterior wall
21. WL, Middle-third greater curve
22. WL, Upper-third greater curvature
23. WL, Upper-third posterior wall
24. WL, Formix
25. WL, Upper-third anterior wall
26. WL, Cardias
27. WL, Esophageal hiatus in retroflexion
28. WL, Upper-third, lesser curvature
29. WL, Middle-third lesser curvature
30. WL, Lower-third lesser curvature
31. WL, Angle
32. WL, Angle, anterior wall
33. WL, Angle, posterior wall
34. WL, Duodenal bulb
35. WL, Duodenum, second portion
36. WL, Duodenum, third portion
37. NBI, Pyloric ring
38. NBI, Antrum, anterior wall
39. NBI, Antrum, lesser curvature
40. NBI, Antrum, posterior wall
41. NBI, Antrum, greater curvature
42. NBI, Antrum-middle-third anterior wall
43. NBI, Antrum-middle-third lesser curvature
44. NBi, Antrum-middle-third posterior wall
45. NBI, Antrum-middle-third greater curvature
46. NBI, Middle-third anterior wall
47. NBI, Middle-third lesser curvature
48. NBI, Middle-third posterior wall
49. NBI, Middle-third greater curve
50. NBI, Upper-third greater curvature
51. NBI, Upper-third posterior wall
52. NBI, Formix
53. NBI, Upper-third anterior wall
54. NBI, Cardias
55. NBI, Esophageal hiatus in retroflexion
56. NBI, Upper-third, lesser curvature
57. NBI, Middle-third lesser curvature
58. NBI, Lower-third lesser curvature
59. NBI, Angle
60. NBI, Angle, anterior wall
61. NBI, Angle, posterior wall
62. NBI, Duodenal bulb
63. NBI, Duodenum, second portion
64. NBI, Duodenum, third portion
65. IC, Duodenum, third portion
66. IC, Duodenum, second portion
67. IC, Duodenal bulb
68. IC, Pyloric ring
69. IC, Antrum, anterior wall
70. IC, Antrum, lesser curvature
71. IC, Antrum, posterior wall
72. IC, Antrum, greater curvature
73. IC, Antrum-middle-third anterior wall
74. IC, Antrum-middle-third lesser curvature
75. IC, Antrum-middle-third posterior wall
76. IC, Antrum-middle-third greater curvature
77. IC, Middle-third anterior wall
78. IC, Middle-third lesser curvature
79. IC, Middle-third posterior wall
80. IC, Middle-third greater curve
81. IC, Upper-third greater curvature
82. IC, Upper-third posterior wall
83. IC, Formix
84. IC, Upper-third anterior wall 85. IC, Cardias
86. IC, Esophageal hiatus in retroflexion
87. IC, Upper-third, lesser curvature
88. IC, Middle-third lesser curvature
89. IC, Lower-third lesser curvature
90. IC, Angle
91. IC, Angle, anterior wall
92. IC, Angle, posterior wall
93. IC. Lower third
94. IC, Mid-third
95. IC, Upper third
96. Lu, Esophagus, lower third
97. Lu, Esophagus, middle third
98. Lu, Esophagus, upper third
99. WL, Hypopharynx
100. WL Left NBI, Pyriform sinus
101. WL, Right Pyriform sinus Uvula
102. WL, hard palate Abbreviations: NBi: Narrow band image. WL: white light. IC: indigo carmine 0.25%. Lu: Lugol The present invention also incorporates new terminology for SCC and every small segment of the imaged organ is alphanumeric coded. An exact description and anatomical location of areas/lesions are further provided via identification of angles, degrees of inclination and length of insertion of the endoscope during the endoscopic examination.

SCC also uses anatomical landmarks, identification of small areas by naming every point observed in an endoscopic view (viewing the endoscopic circumference like a round clock), reports the depth of insertion based on the endoscope length and uses natural or handmade endoscopic axis or angles (hand-manipulated from outside by moving the endoscope's wheels or by the endoscopist's hand-turning). Preferred embodiments of the invention comprise use of this new medical terminology to report/describe SCC, to record any abnormalities, to precisely locate a condition or an early lesion, to effectively design the way of endoscopic removal of a cancer and for effective follow up even for a different examiner.

The sequence, names and numbers of each segment are as follows.
1. Terminal ileum
2. Cecum
3. Ascending colon distal third
4. Ascending colon middle third
5. Ascending colon proximal third
6. Hepatic flexure (seen from the transverse colon)
7. Proximal Transverse
8. Middle transverse (Mid-T)
9. Distal transverse
10. Splenic flexure seen from the descending colon
11. Proximal descending colon
12. Middle descending colon
13. Distal descending colon
14. Sigmoid-descending angle
15. Proximal sigmoid
16. Middle sigmoid
17. Distal sigmoid
18. Recto-sigmoid angle
19. Proximal rectum
20. Middle rectum
21. Distal rectum
22. Distal rectum in retroflex view
23. Anal channel During endoscope retrieval while the patient is lying in left lateral decubitus supine position, water/fecal residual liquid naturally flows downward. In all the portions of the colon (cecum, ascending colon, transverse, descending, sigmoid, rectum) when the lumen is divided into four quadrants this quadrant/side corresponds to the posterior wall. Therefore its opposite side corresponds to the anterior wall. In addition, based on anatomy landmarks the quadrant located to the left (clockwise rotation) of the posterior wall corresponds to the mesenteric wall and its opposite corresponds to the anti-mesenteric wall.

The inventive electronic colon scope uses similar principles to SCE although the longitudinal line along the shaft coupled with the mouthpiece might not be necessary. * A similar instrument a rectal piece may be adapted to measure angles in a similar way to the technique used for SCR* When performed digitally the grades of torque applied to the shaft or to the endoscope head will permit efficient angulation and effective maneuvers which are useful for performing the Emura insertion technique and also for retrieval.

SCE/SCC uses both electronic (e.g. NBI, FICE or any other) and conventional chromoendoscopy (indigo carmine, Lugol) and/or any other colorant/dye that enhances the microanatomy of the stomach, colon or any other organ. Chromoendoscopy provides remarkable enhancement of the surface microanatomy and provides the endoscopist with a much better view of the lesion in order to perform biopsy/resection/burning or to destroy in any other manner the lesion aiming to diagnose/cure/palliate symptoms in a given patient.

The method and system of the present invention has various applications. Some of the applications of this new medical terminology are to establish global report standardization, to understand endoscopic anatomy of the selected organ, to describe SCE, to record abnormalities (if any), to precisely locate a condition or an early lesion, to effectively design and implement endoscopic removal of a cancer and for effective follow up even for different examiners.

In vivo digital/electronic positioning of the endoscope tip involves electric/magnetic/echo/internet signaling originating from or to the tip of the endoscope to or from a monitor/processor and, measured by angles (from 0° to 360°) that signals the exact position in grades as north, south, west, east or a mix of these (e.g. southeast, northwest). Thus, image reconstruction involves a digitalized model resembling the organ imaged plus the image of the endoscope within the organ. On the other hand, input signaling from the processor/device to the endoscope enables the examiner to manipulate the insertion distance, the wheels grade movements, the shaft rotation and, ultimately, to achieve complete control of the endoscope tip movement. Manipulation is externally controlled by hand or other controllable device and allows performing virtual/non-presential endoscopic procedures (referred to herein as "tele-endoscopy/robotic endoscopy/satellital endoscopy") by manipulating the controls/movement of the endoscope tip through an electronic/programmed digitized system operated virtually/non-presentially by the examiner.

Referring to FIG. 1, shown is an illustrative view of the present invention in use. The present invention provides an endoscopic system 10 systematic process whereby medical personnel, whether an endoscopist or not, performs a stepped process for imaging internal organs of a patient 12 and recording a descriptor taken from a set of universal terminology so that any medical professional can easily locate the target area. The process provides a much higher precision of the anatomical location of lesions and description and is thereby more reproducible. Shown is the endoscopic system 10 of the invention including an endoscope 14, an angulation adapter 16 and a graduated endoscope shaft 18 connected to a processor 20. The images can be transmitted by mail or the internet 22 to an authoritative medical professional for interpretation, report, a second look, local resection or open resection by general surgery, and can be viewed on a display 24. As used herein, the term "endoscopy" refers to both endoscopy and colonoscopy.

Figure 2:
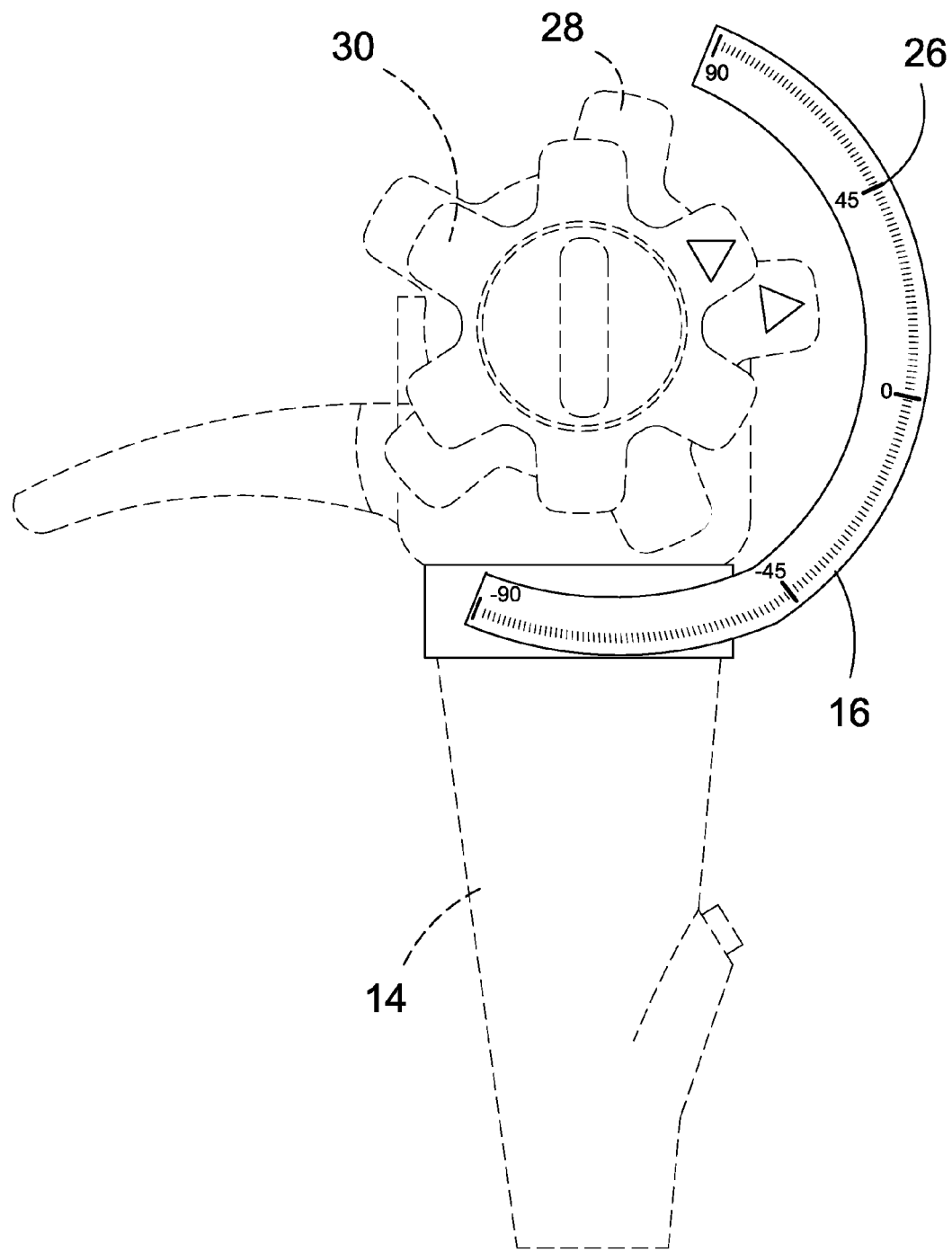
FIG. 2 is front view of the angulation adapter in use.

Referring to FIG. 2, shown is a front view of the angulation adapter 16 in use. Shown is the angulation adapter 16 mounted on a typical endoscope' head 14 providing means for recording coordinates in positive and negative degrees for both left and right movement and up and down movement for a given target location. The angulation adapter 16 is a semi-circular device with markings 26 in grades (a section of 0 to 360° circumference) located parallel and in between the up-down wheel 28 and the left-right wheel 30 that informs the endoscopist of the degree of R&L, U&D wheel rotation, providing for a system of coordinates that makes the procedure reproducible as well as facilitating following up on suspicious lesions.

Figure 5:
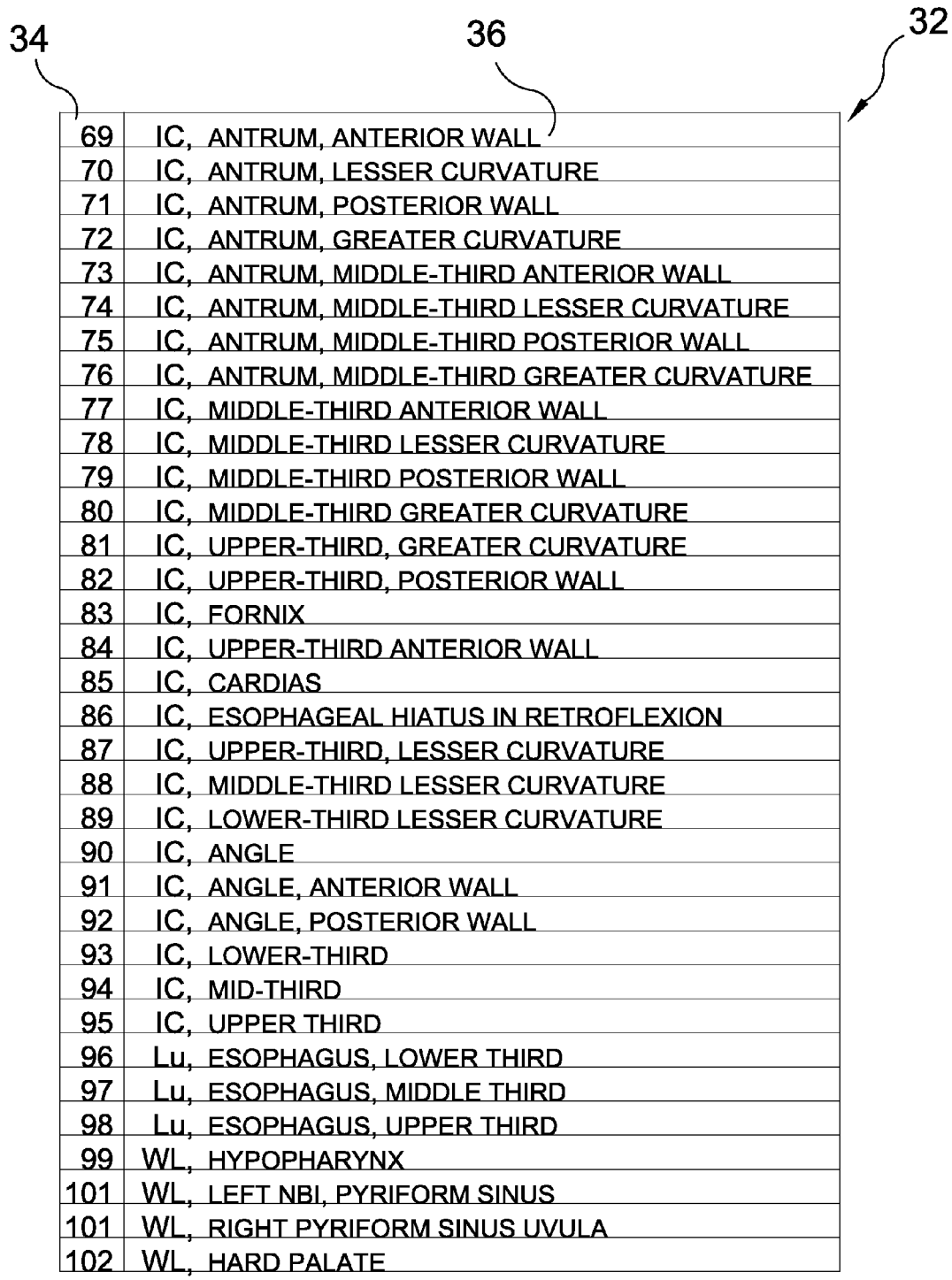
FIG. 5 is a continuation of the chart exemplifying universal terminology for the upper GI tract.

Referring to FIGS. 3 thru 5, shown is a chart 32 exemplifying universal terminology for the upper GI tract. Depicted is a list of universal terminology reference numbers 34 each of which is associated with a universal terminology location descriptor 36 that are applied to images describing the anatomical location of an image and the type of light used in rendering the image.

Figure 6:
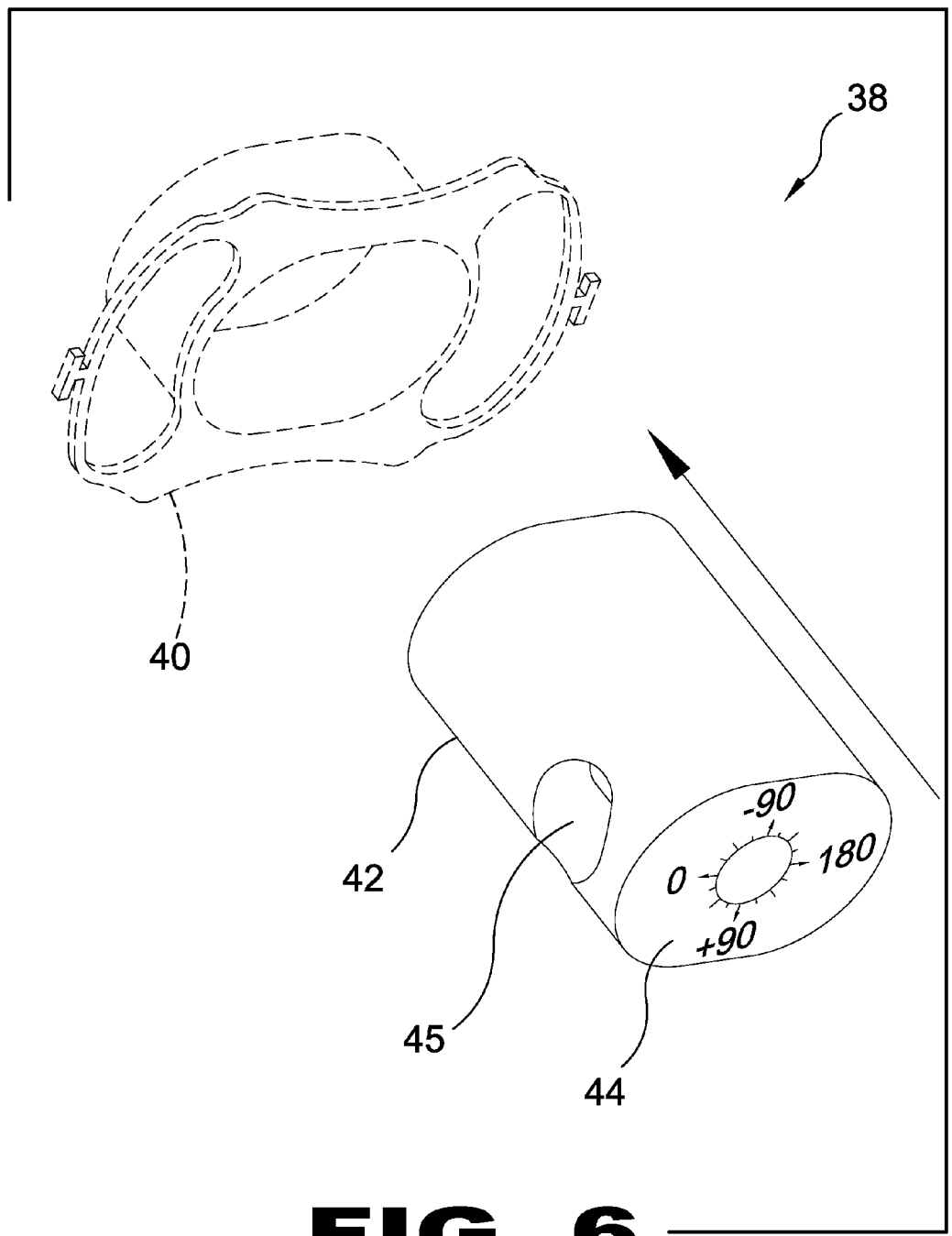
FIG. 6 is a perspective view of the intelligent mouthpiece of the present invention.

Referring to FIG. 6, shown is a perspective view of the intelligent mouthpiece 38 of the present invention. The present invention provides a mouthpiece 38 to measure the inclination of the scope in relationship to a patient's plane, i.e. coronal or sagittal. The mouthpiece 38 provides an easy and reproducible way (even for beginners and non-endoscopists) of performing systematic chromoendoscopy and to properly identify target areas. The intelligent mouthpiece 38 includes standard mouthpiece 40 and a sleeve 42 with marks 44 at 0, ±45, ±90, ±135 and ±180 degrees to measure the grades of inclination of the endoscope having the patient as reference. The sleeve 42 of the intelligent mouthpiece 38 attaches to the standard mouthpiece 40 and incorporates a lateral orifice 45 for drainage or suction.

Figure 7:
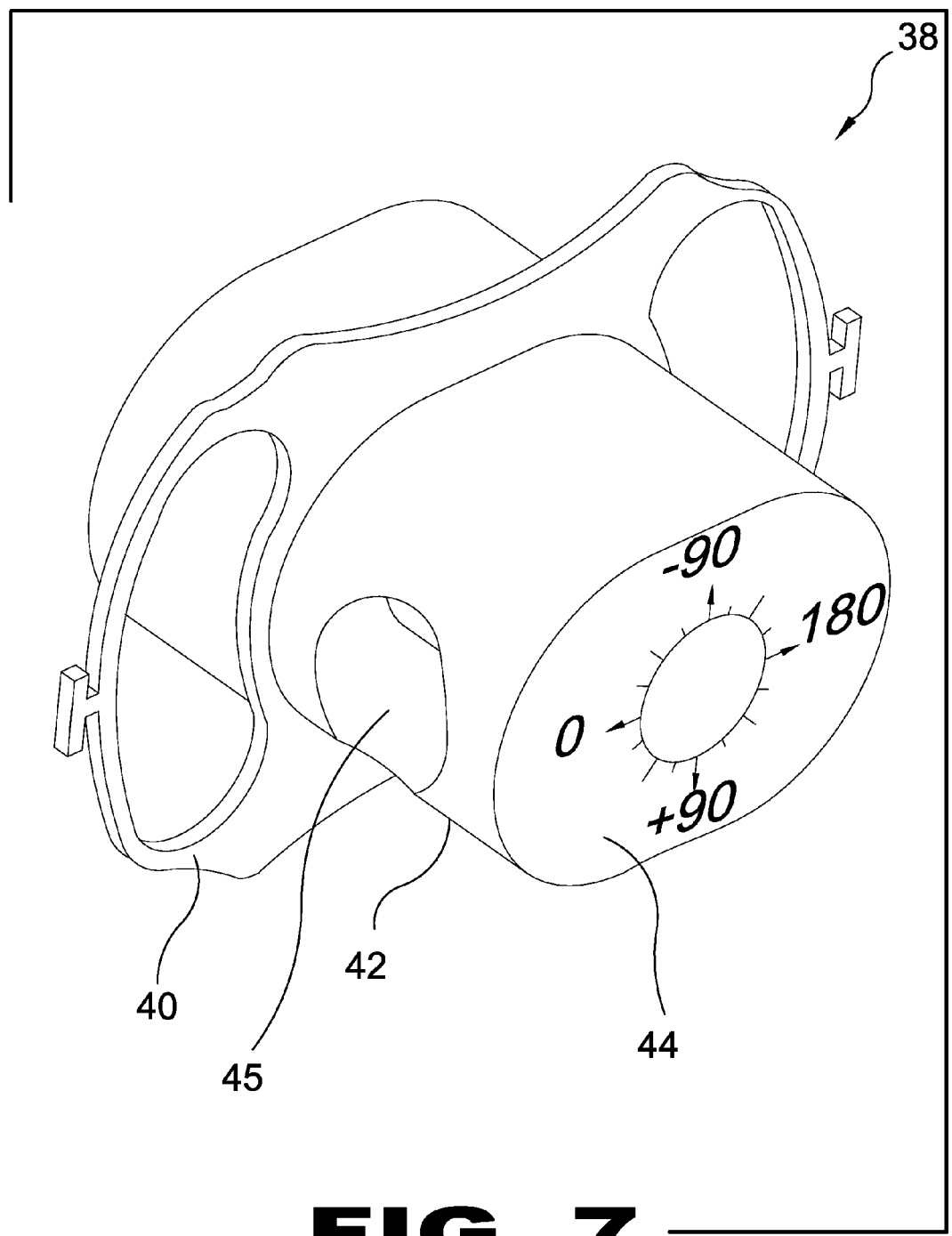
FIG. 7 is a perspective view of the intelligent mouthpiece of the present invention.

Referring to FIG. 7, shown is a perspective view of the intelligent mouthpiece 38 of the present invention. The present invention provides a mouthpiece 38 to measure the inclination of the scope in relationship to a patient's plane, i.e. coronal or sagittal. The mouthpiece 38 provides an easy and reproducible way (even for beginners and non-endoscopists) of performing systematic chromoendoscopy and to properly identify target areas. The intelligent mouthpiece has a sleeve 42 with marks 44 at 0, ±45, ±90, ±135 and ±180 degrees to measure the grades of inclination of the endoscope having the patient as reference. The sleeve 42 of the intelligent mouthpiece 38 attaches to a standard mouthpiece 40 and incorporates a lateral orifice 45 for drainage or suction.

Figure 8:
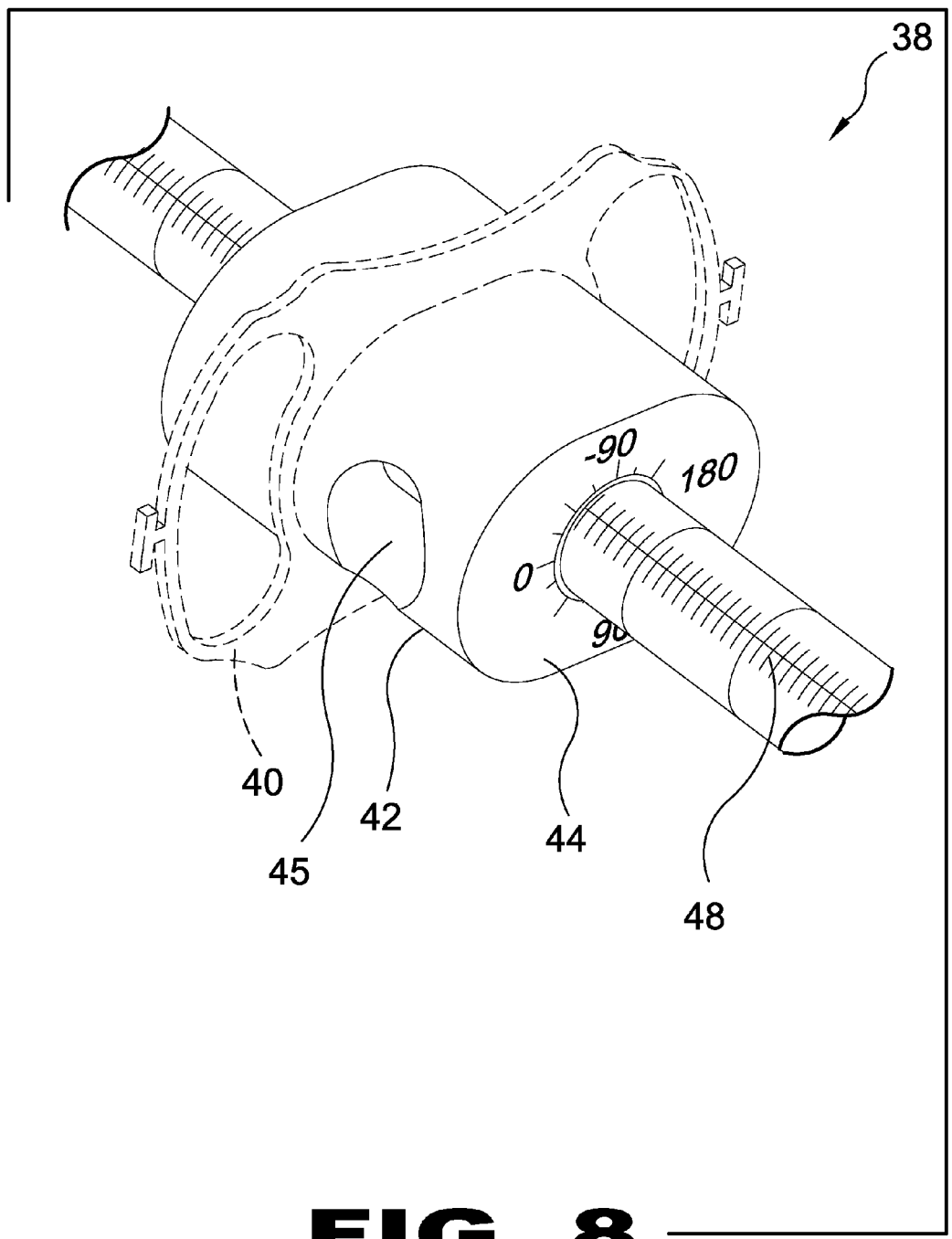
FIG. 8 is a perspective view of the intelligent mouthpiece of the present invention.

Referring to FIG. 8, shown is a perspective view of the intelligent mouthpiece 38 of the present invention. The present invention provides a shaft 46 having graduated marks 48 on both sides with two longitudinal lines 180 degrees apart as a point of reference of the rotation of the device that works in conjunction with the mouthpiece 38 to measure the inclination of the scope in relationship to a patient's plane, i.e. coronal or sagittal. The intelligent mouthpiece has a sleeve 42 with marks 44 at 0, ±45, ±90, ±135 and ±180 degrees to measure the grades of inclination of the endoscope. The sleeve 42 of the intelligent mouthpiece 38 attaches to a standard mouthpiece 40 measure 1 cm from the standard mouth piece to the proximal verge and incorporates a lateral orifice 45 for drainage or suction.

Figure 9:
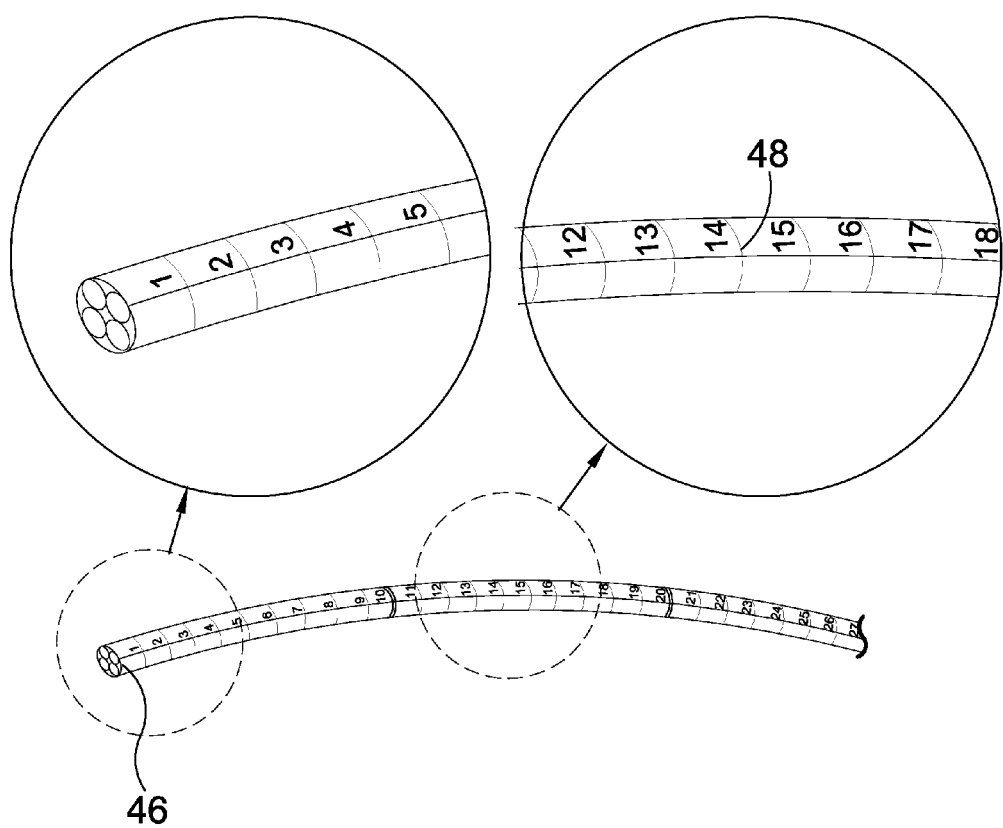
FIG. 9 is a perspective view of the endoscope shaft of the present invention.

Referring to FIG. 9, shown is a perspective view of the endoscope shaft 46 of the present invention. The present invention provides a shaft 46 having graduated marks 48 on both sides with two longitudinal lines 180 degrees apart as a point of reference of the rotation of the device that works in conjunction with the mouthpiece to measure the inclination of the scope in relationship to a patient's plane, i.e. coronal or sagittal. While the graduations are illustrated in whole numbers, the present invention provides for very precise measurements including fractions of a centimeter.

Figure 10:
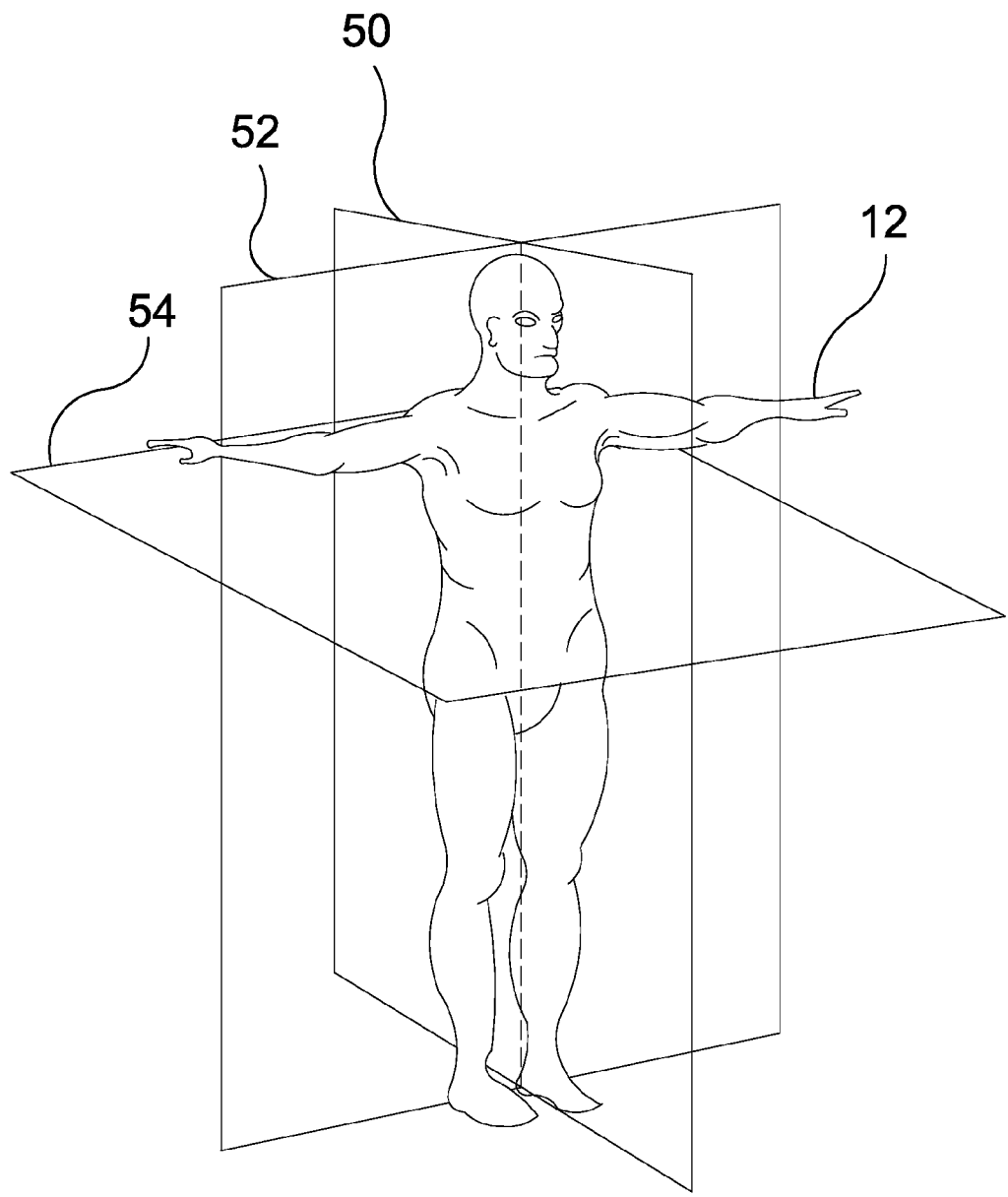
FIG. 10 is an illustrative view of the patient's planes.

Referring to FIG. 10, shown is an illustrative view of the patient's plane. Shown is a graphical depiction of a patient 12 divided into sagittal plane 50, coronal plane 52 and transverse plane 54. The present invention provides a systematic process whereby medical personnel perform a stepped process for imaging internal organs and recording a descriptor taken from a set of universal terminology so that any medical professional can easily locate the target area. The process provides a much higher precision of the anatomical location of lesions and description thereby more reproducible.

Figure 11:
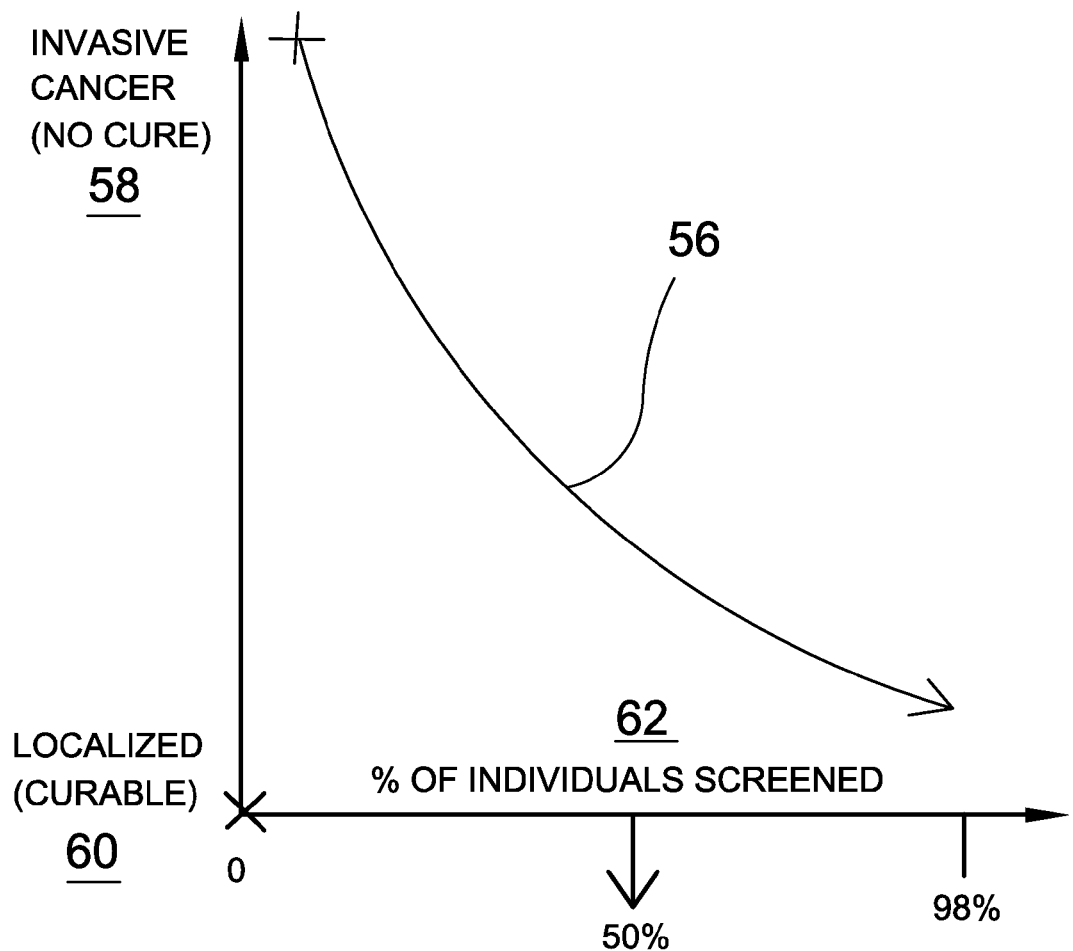
FIG. 11 is a graph illustrating the advantage of the present invention.

Referring to FIG. 11, shown is a graph illustrating the advantage of the present invention. Shown is a graphical plot 56 showing a decrease in invasive cancer 58 detections, as opposed to localized condition 60 detections, as the number of population screened 62 is increased. Statically localized cancer of the stomach is found in approximately 1/360 healthy individuals. Regardless of the organ or disease, more screened individuals in a timely manner will result in earlier detection and higher possibility of cure. Therefore, the systemization of endoscopic examination, with the aid of the coordinate system, will maximize use of resources and allow for a wider population to be screened, which will translate in earlier detection of tumors and treatment that will be curative without the need of a partial resection of the organ.

Figure 12:
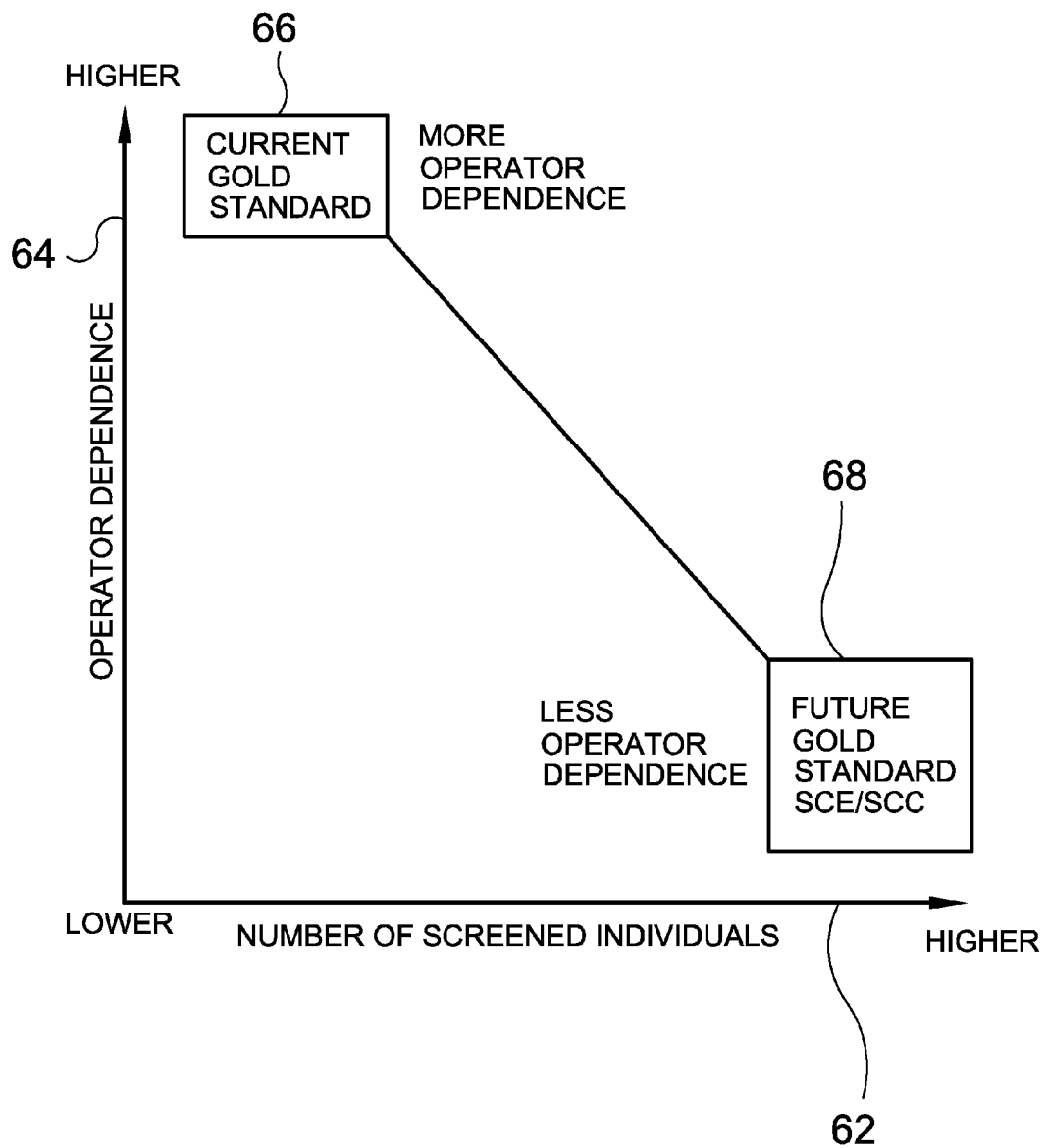
FIG. 12 is a chart illustrating the relationship between operator dependence and number of screened individuals.

Referring to FIG. 12, shown is a chart illustrating the relationship between operator dependence 64 and the number of screened individuals 62. A significant limitation to mass screening campaigns is the higher operator dependence 66 of the prior art endoscopy methods, which limits the number of individuals 62 who can be screened. The present invention results in lower operator dependence 68 and increases the number of individuals 62 who can be screened via systematic chromoendoscopy (SCE) and systematic chromocolonoscopy (SCC).

Figure 13:
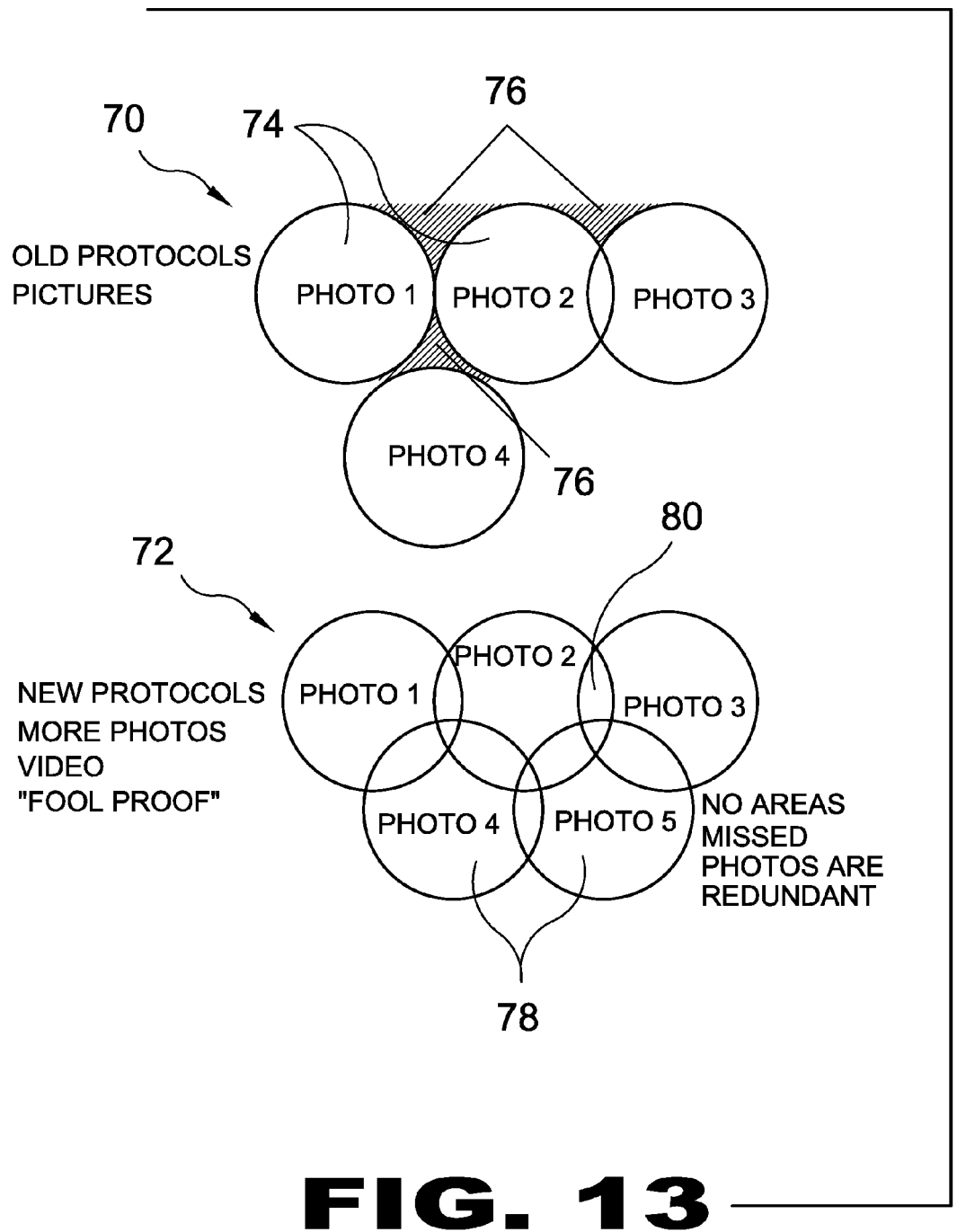
FIG. 13 is an illustration of the comprehensive, overlapping imaging provided by the present invention.

Referring to FIG. 13, shown is an illustration of the comprehensive, overlapping imaging provided by the present invention. Shown are the prior art protocols imaging system 70 and the new protocol imaging system 72 of the present invention. With the prior art protocol 70, the images 74 have gaps therebetween which represent non-imaged portions 76 of the organ being screened. The present invention requires that the images 78 have overlapping portions 80 so that no areas are missed, allowing for less trained personnel to perform the exam, while maximizing the time the expert endoscopic surgeon (EES) or master endoscopic surgeon (MES) is used. These redundant pictures will allow in the near future for imaging software to be developed under our protocols and coordinate systems and reconstruct the organs whole surface with micro-anatomic resolution, to then, be presented in a film, or set of films. To the SES, this adds an additional level of foolproofing. The software will show gaps if visual information was not obtained. i.e. a section was skipped. It can also start the process at the same time the exam is being down. Thus if a section of the organ is missing it can be completed without the need of a new exam. The software will have imbedded coordinate information and can guide the operator to the area that he needs to image (less operator dependence)

once the films are obtained, they can be transmitted digitally in a way similar to the way virtual radiology services operate (a radiologist in Australia does the radiology for Florida in the middle of the night), or they can be printed and given to the EES or MES time, but could be produced by us in the future)

Figure 14:
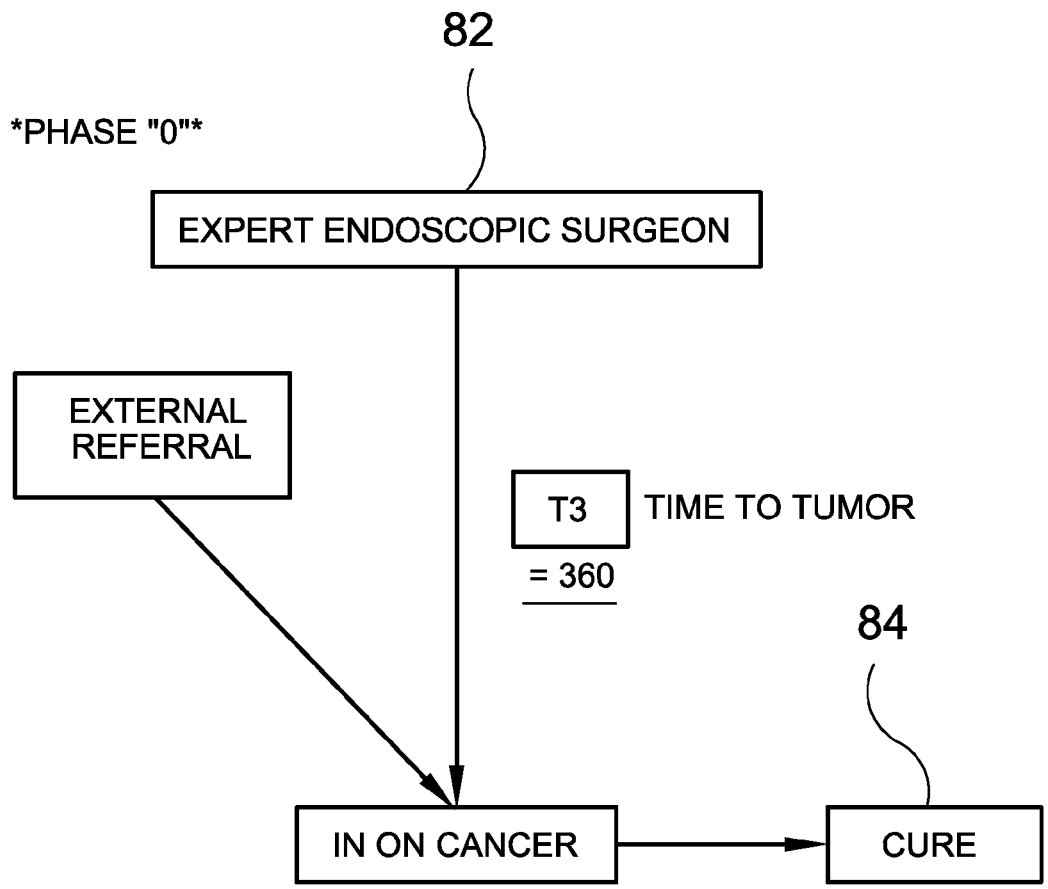
FIG. 14 is a flow chart illustrating Phase 0 of the present invention.

Referring to FIG. 14, shown is a flow chart illustrating Phase 0 of the present invention. The present invention allows for decreased operator dependence, reduced cost and improved utilization of local resources, and is expected to significantly reduce the time-to-tumor (ttt or t3). In Phase 0, the current phase, the expert endoscopic surgeon 82 does almost all of the screening exams. As illustrated in FIG. 14, approximately 1 localized cancer is detected for each 325 exams in high risk populations. The present invention will allow the expert endoscopic surgeon 82 to spend more time providing cures 84 for early detected localized conditions.

Figure 15:
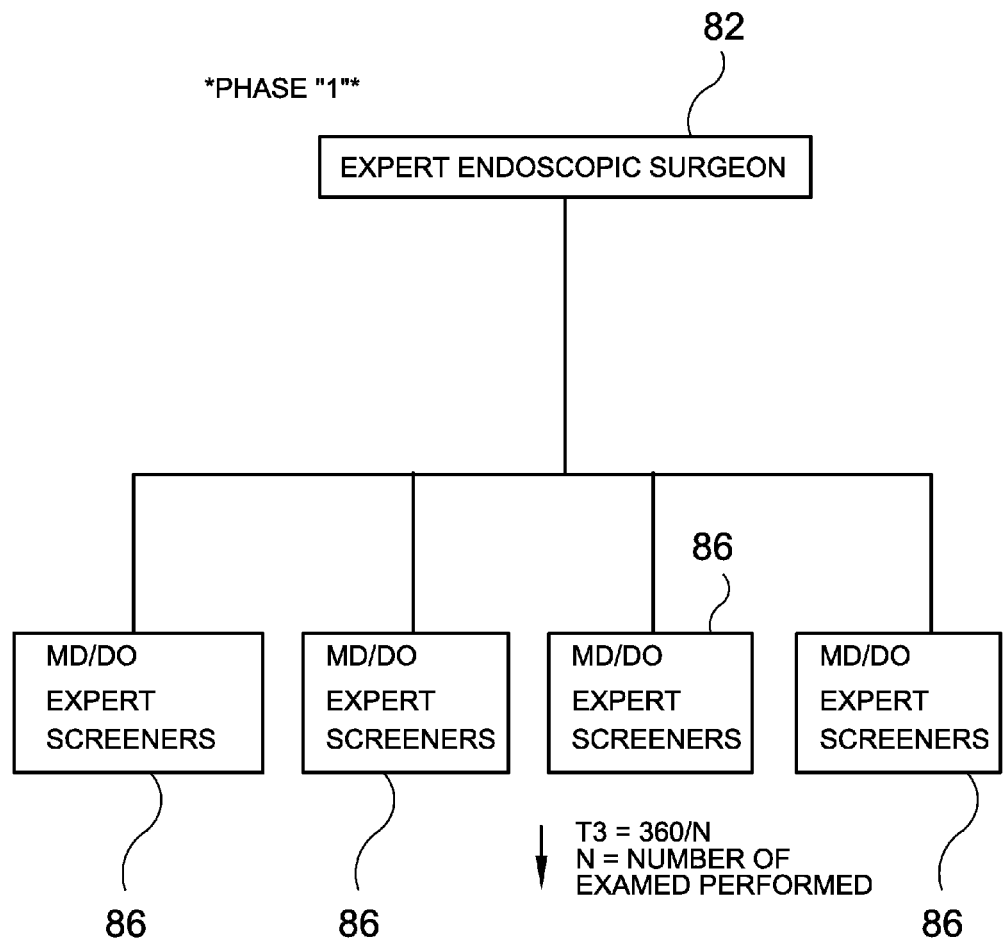
FIG. 15 is a flow chart illustrating Phase 1 of the present invention.

Referring to FIG. 15, shown is a flow chart illustrating Phase 1 of the present invention. In phase 1, the expert endoscopic surgeon 82 oversees a number of expert screeners that perform SCC/SCE, thus time to tumor is reduced proportionally to the number of screeners. For example, by increasing the number of screeners by a factor of 10, localized cancer can be found 10 times more often, saving 10 times as many lives. The expert screeners can include M.D. expert screeners 86 and non-M.D. expert screeners 88.

Figure 16:
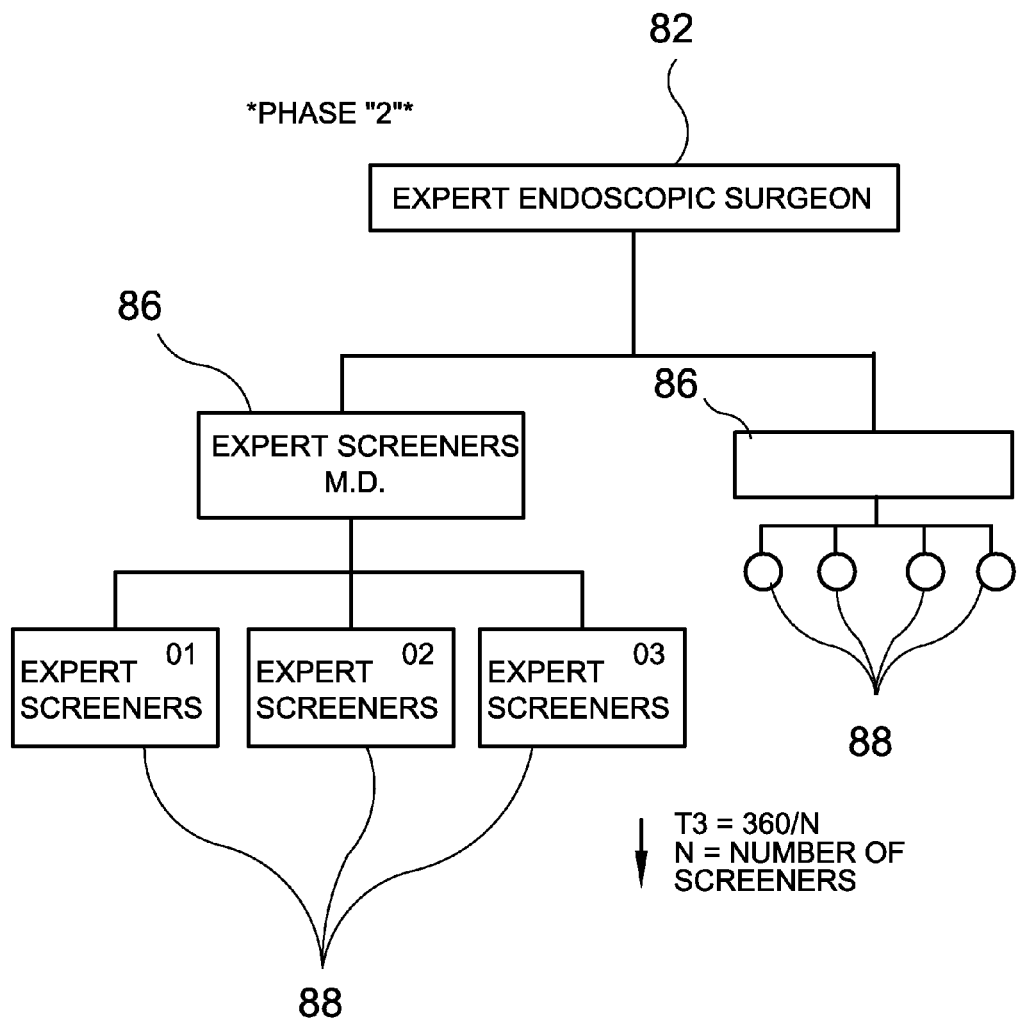
FIG. 16 is a flow chart illustrating Phase 2 of the present invention.

Referring to FIG. 16, shown is a flow chart illustrating one embodiment of Phase 2 of the present invention. In Phase 2, the expert endoscopic surgeon 82 supervises one or more can be general practitioners, mid-levels or M.D. expert screeners 86, who, in turn, supervise one or more other expert screeners 90, thus allowing the expert endoscopic surgeon 82 more time for performing surgical procedures such as resection 92 of localized tumors. In time the expert screeners may become expert screeners supervisors, which will result in greater number of screeners and over years the cost to produce expert screeners will dramatically come down thus allowing for a lower cost to society and a much faster implementation of mass application campaigns.

Figure 17:
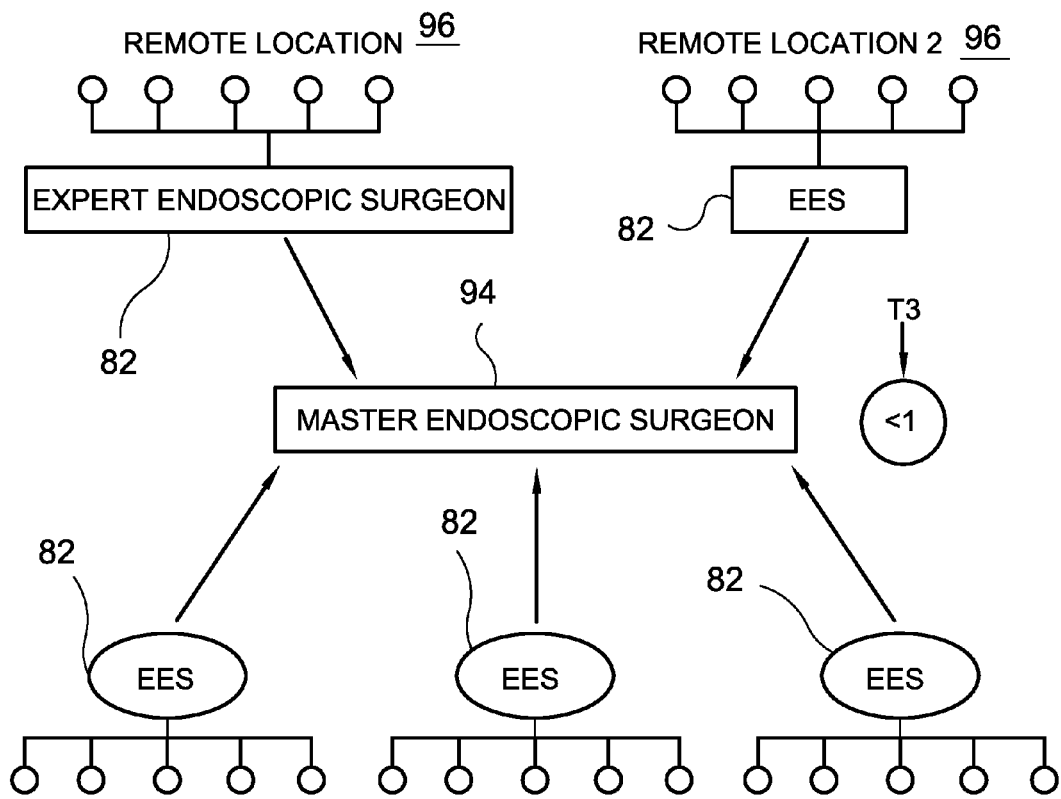
FIG. 17 is a flow chart illustrating Phase 3 of the present invention.

Referring to FIG. 17, shown is a flow chart illustrating Phase 3 of the present invention. In Phase 3, the expert endoscopic surgeons 82 are supervised by a master endoscopic surgeon (MES) 94, who can monitor the expert endoscopic surgeons 82 at remote locations 96 in different states or countries. The MES 94 is able to supervise cases from remote locations 96 and if needed can perform surgery remotely via tele-medicine. The expert endoscopic surgeons 82 may oversee a local city/area/state screening operation.

Figure 18:
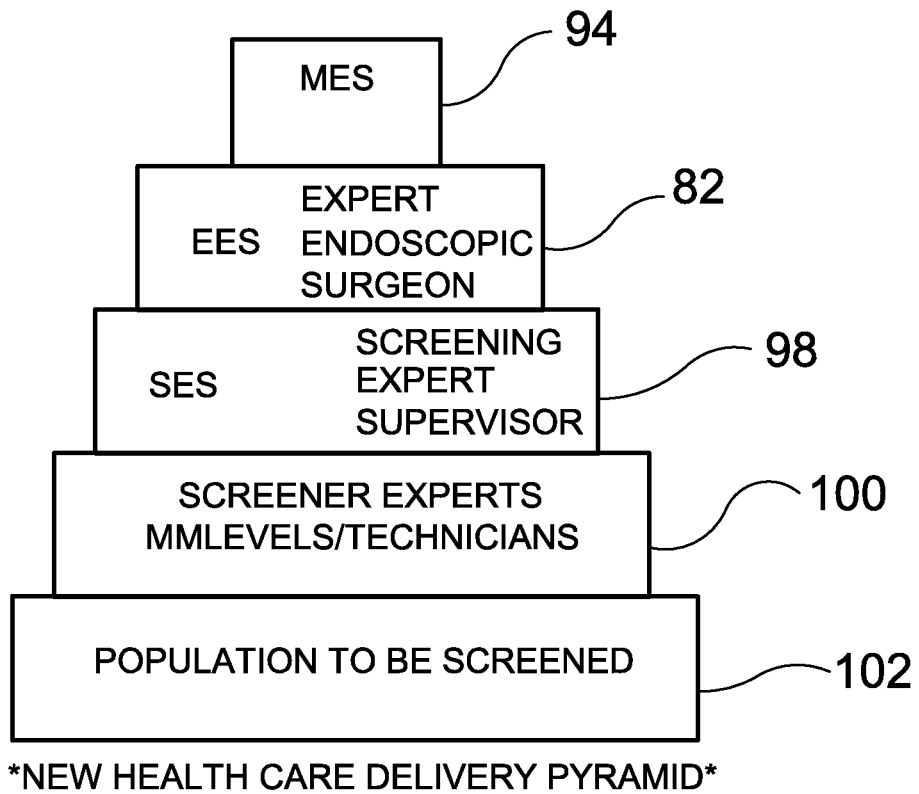
FIG. 18 is a depiction of the new health care delivery pyramid of the present invention.

Referring to FIG. 18, illustrated is a new health care delivery pyramid for GI cancers and other cancers that can use a systematic endoscopic approach. The master endoscopic surgeon 94 is at the top of the pyramid, followed in order by one or more expert endoscopic surgeons 82, screening expert supervisors 98 and screener experts 100, allowing for a much higher population to be screened 102.

Referring to FIGS. 19A thru 19B, shown is a chart of the coordinate system. The coordinate system either analog or digital of the present invention can increase reproducibility of the exam, and once digitalized can be transmitted to a remote place to allow for tele-medicine operations. In addition a new medical endoscopy nomenclature describe every part/portion located within a specific organ.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. An endoscopic apparatus comprising:
   a) an endoscope having an upper/lower wheel and a right/left wheel for controlling bending of an endoscope tip within an organ being imaged;
   b) a mouthpiece adapted to measure inclination of said endoscope using a patient's incisor teeth as reference and having marks at every degree starting at 0 and going to 360, with 0 degrees oriented at the front of the patient in an anatomical plane, said mouthpiece having an electronic device for digitally measuring inclination and depth of a tip of said endoscope;
   c) an endoscope shaft having a plurality of marks along a longitudinal length of said shaft for digitalization of output to precisely obtain the length of insertion from a reference point to a tip of said endoscope, said endoscope allowing exact description and anatomical location of a lesion by measuring grades of inclination, depth of insertion and tip positioning;
   d) an angulation device adapted to measure rotation of said upper/lower and right/left wheels;
   e) a longitudinal mark at said endoscope tip and along said shaft of said endoscope for measuring inclination in degrees at any moment during an examination;
   f) a processor for receiving and processing imaging data from said endoscope, wherein movement of said wheels releases signals which are delivered to said processor and said processor reconstitutes said signals into a tridimensional image; and
   g) endoscopic systems of coordinates which are digitalized allowing for real time monitoring of position and provide feedback to the operator, with said coordinate information recorded in real time in each image.

* * * * *